(12) United States Patent
Saito

(10) Patent No.: US 9,345,392 B2
(45) Date of Patent: May 24, 2016

(54) ENDOSCOPE SYSTEM AND METHOD FOR IMAGING EXPOSURE CONTROL

(71) Applicant: FUJIFILM CORPORATION, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 343 days.

(21) Appl. No.: 13/779,006

(22) Filed: Feb. 27, 2013

(65) Prior Publication Data

US 2013/0245410 A1 Sep. 19, 2013

(30) Foreign Application Priority Data

Mar. 14, 2012 (JP) ................. 2012-057285

(51) Int. Cl.
*A61B 1/06* (2006.01)
*A61B 1/045* (2006.01)
(Continued)

(52) U.S. Cl.
CPC .............. *A61B 1/045* (2013.01); *A61B 1/0002* (2013.01); *A61B 1/00009* (2013.01); *A61B 1/0051* (2013.01); *A61B 1/043* (2013.01); *A61B 1/0638* (2013.01); *A61B 5/1459* (2013.01); *A61B 5/14556* (2013.01); *A61B 1/0005* (2013.01); *A61B 1/0653* (2013.01)

(58) Field of Classification Search
CPC .... A61B 1/0638; A61B 1/063; A61B 1/0646; A61B 1/0005; A61B 1/00186; A61B 1/05; A61B 1/00009; A61B 1/045; A61B 1/07; G06T 2207/10068; G06T 2207/10144; G06T 2207/30101; G06T 5/50
USPC .......................... 600/109, 180, 323, 331, 339
See application file for complete search history.

(56) References Cited

U.S. PATENT DOCUMENTS 8,535,221 B2 * 9/2013 Saito ............................ 600/180
8,938,279 B1 * 1/2015 Heaton et al. ................ 600/323
(Continued)

FOREIGN PATENT DOCUMENTS

EP 1 488 732 A1 12/2004
EP 2 106 736 A2 10/2009
(Continued)

OTHER PUBLICATIONS

An Extended European Search Report, dated Jun. 25, 2013, for Patent Application No. 13156831.3.
(Continued)

*Primary Examiner* — John P Leubecker
*Assistant Examiner* — Arnaldo Torres Diaz
(74) *Attorney, Agent, or Firm* — Birch, Stewart, Kolasch & Birch, LLP

(57) ABSTRACT

In a special observation mode, an oxygen saturation frame period, a normal frame period, and a vessel pattern frame period are repeatedly performed. A brightness detector detects the brightness of a latest frame image of an oxygen saturation video image, being a key video image. The intensity of light to be applied in the next oxygen saturation frame period is determined from the detected brightness. From the determined light intensity and a light intensity ratio among frames, the intensity of light to be applied in the next normal frame period and the next vessel pattern frame period is calculated. The exposure time of the next oxygen saturation frame period is determined from the detected brightness. From the determined exposure time and an exposure time ratio among frames, the exposure time of the next normal frame period and the next vessel pattern frame period is determined.

12 Claims, 20 Drawing Sheets

(51) Int. Cl.
*A61B 1/00* (2006.01)
*A61B 1/005* (2006.01)
*A61B 1/04* (2006.01)
*A61B 5/1455* (2006.01)
*A61B 5/1459* (2006.01)

(56) References Cited

U.S. PATENT DOCUMENTS

| | | |
|---|---|---|
| 2004/0267091 A1 | 12/2004 | Imaizumi et al. |
| 2009/0082650 A1* | 3/2009 | Wilson et al. ............... 600/323 |
| 2009/0247847 A1* | 10/2009 | Pogue et al. ............... 600/323 |
| 2009/0262225 A1 | 10/2009 | Yamaguchi et al. |
| 2010/0256469 A1* | 10/2010 | Cook et al. ............... 600/323 |
| 2011/0069205 A1 | 3/2011 | Kasai et al. |
| 2011/0071353 A1* | 3/2011 | Ozawa ............... A61B 1/0638 600/109 |
| 2011/0237915 A1* | 9/2011 | Yamaguchi ............... 600/339 |

FOREIGN PATENT DOCUMENTS

| | | |
|---|---|---|
| EP | 2 309 457 A1 | 4/2011 |
| EP | 2 368 480 A1 | 9/2011 |
| JP | 11-244229 A | 9/1999 |
| JP | 2003-33324 A | 2/2003 |
| JP | 2011-36361 A | 2/2011 |
| JP | 2012-16545 A | 1/2012 |
| WO | WO 2012/169270 A1 | 12/2012 |

OTHER PUBLICATIONS

Japanese Office Action and English translation thereof, dated Jun. 25, 2014, for Japanese Application No. 2012-057285.

Japanese Office Action dated Jan. 30, 2014, issued in corresponding Japanese Parent Application No. 2012-057285.

European Office Action, issued Jul. 28, 2015, for European Application No. 13156831.3.

* cited by examiner

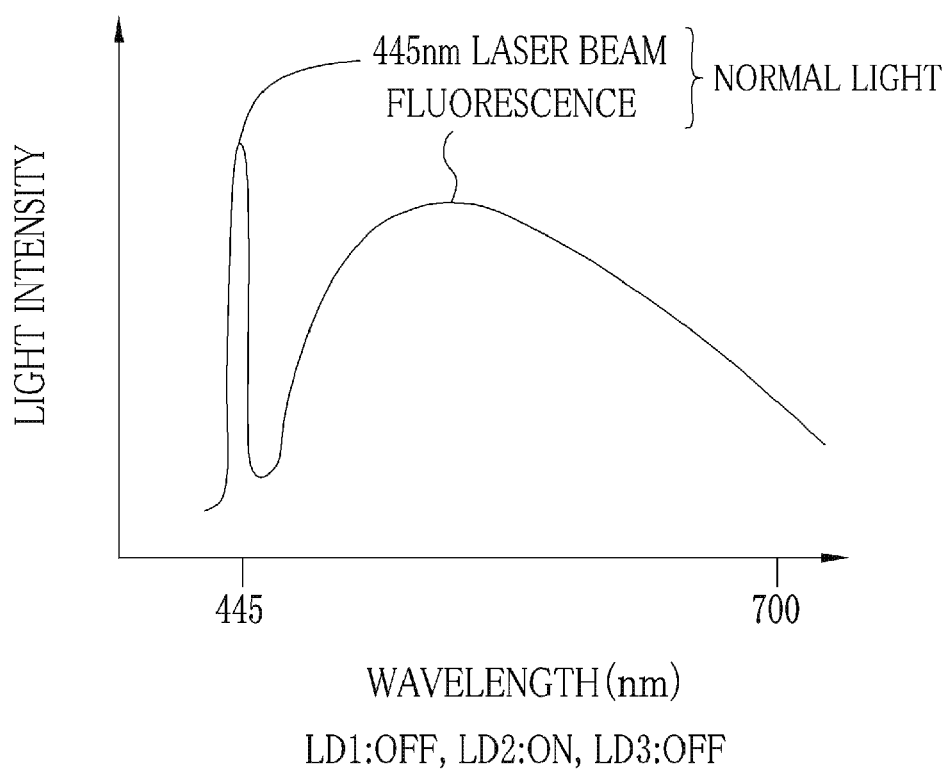

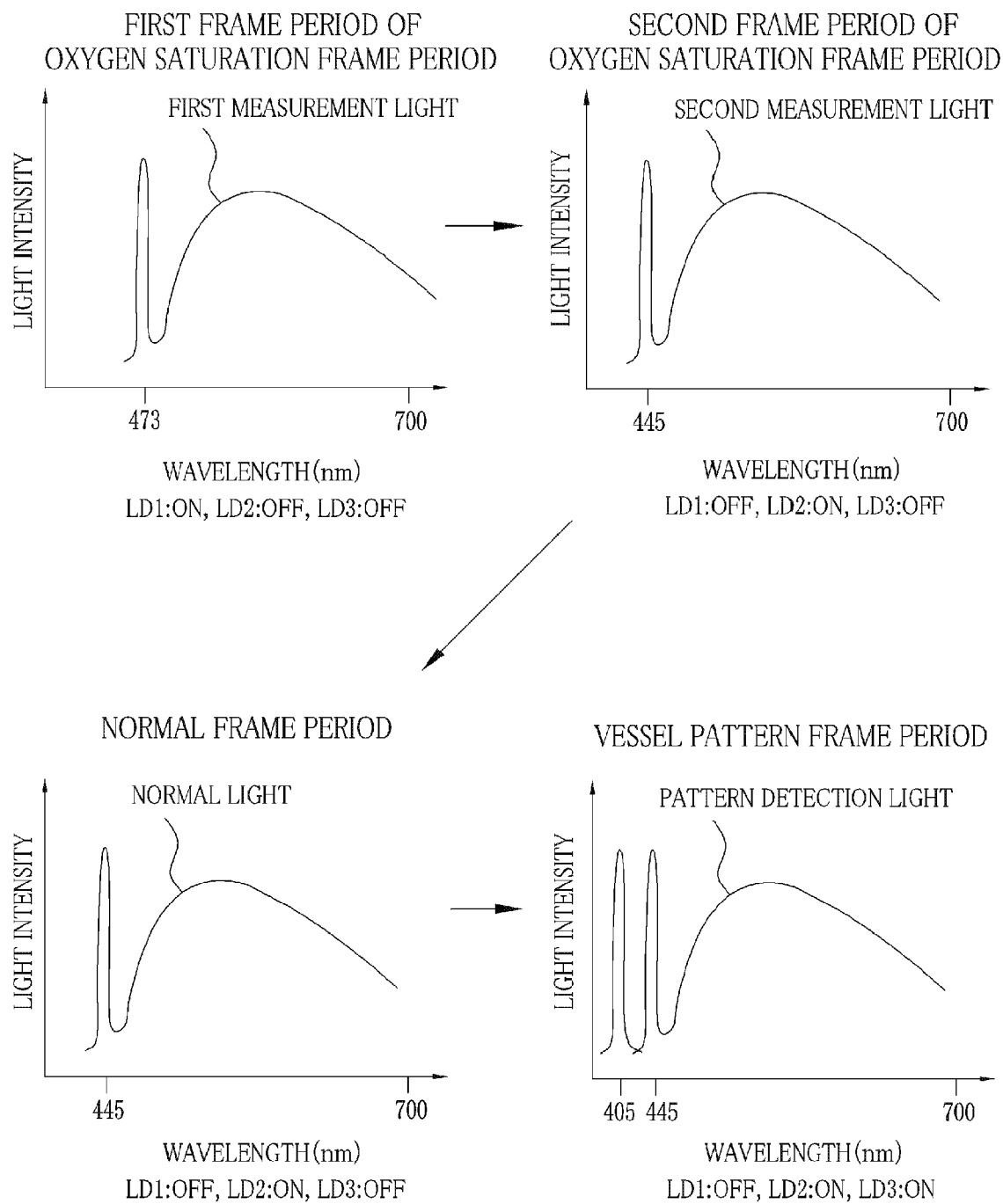

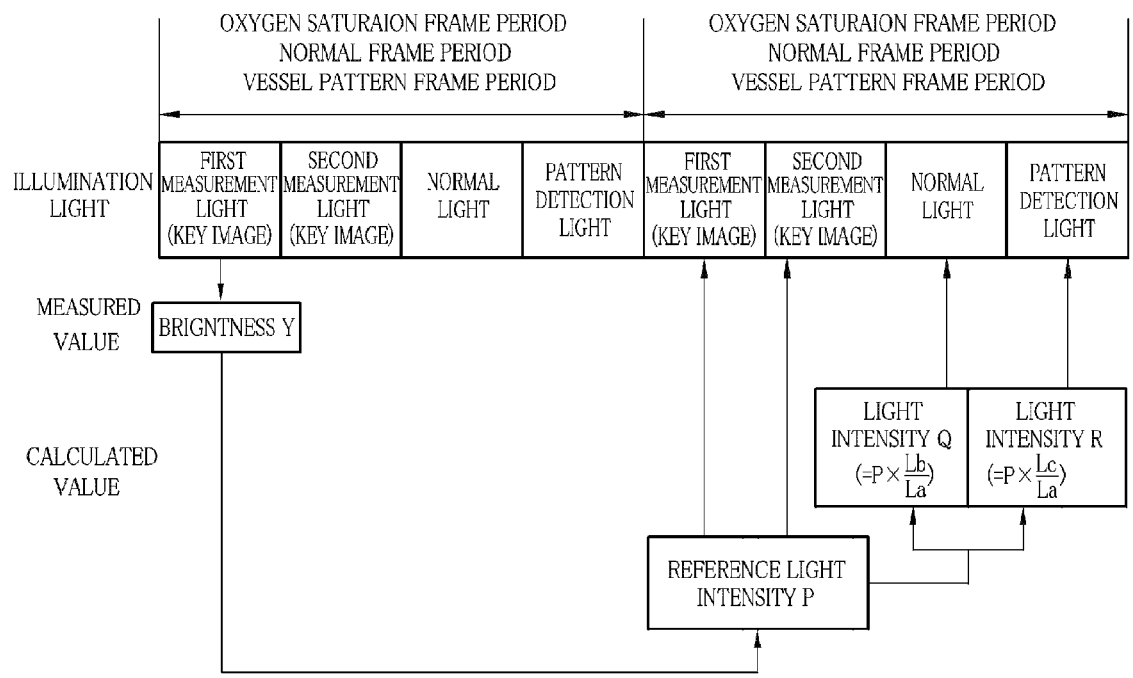

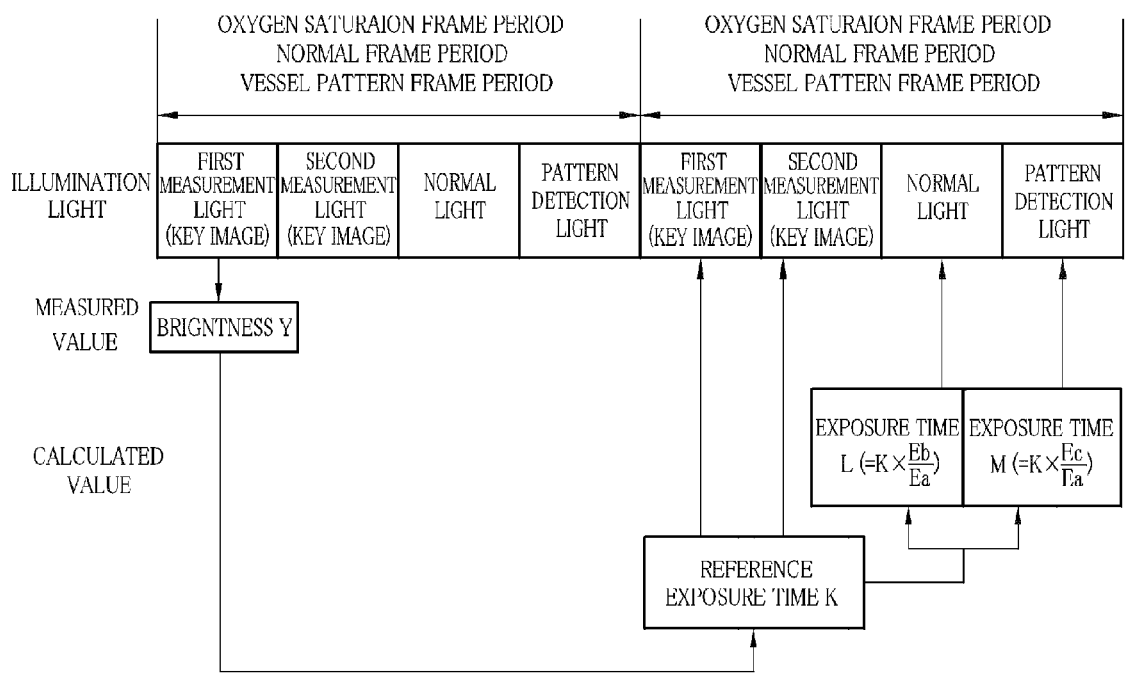

ENDOSCOPE SYSTEM AND METHOD FOR IMAGING EXPOSURE CONTROL

BACKGROUND OF THE INVENTION

1. Field of the Invention

The present invention relates to an endoscope system that produces not only a normal video image captured under normal light but also a special video image captured under special light, a processor device of the endoscope system, and an exposure control method.

2. Description Related to the Prior Art

An endoscope system is widely used in examination of the interior of a patient's body, e.g. a digestive system. The endoscope system is constituted of an electronic endoscope to be introduced into the patient's body, a light source device for supplying illumination light to the electronic endoscope, a processor device for processing an image (video image) captured by the electronic endoscope, and a monitor for displaying the image after being processed by the processor device. In recent years, there is known an endoscope system that carries out not only normal observation for imaging an internal body portion under white light (normal light) but also special observation for imaging the internal body portion irradiated with specific narrowband light (special light).

As the special observation, a blood vessel pattern obtaining technique is known in which a blood vessel in a specific depth is emphasized by applying the special light that has a wavelength having a high light absorption coefficient of hemoglobin to the internal body portion. Whether or not an obtained blood vessel pattern matches with a pattern specific to cancer is judged to find out a cancer-suspected lesion.

Also, there is known an oxygen saturation level obtaining technique. This technique uses first illumination light being narrowband light in a wavelength band at which a light absorption coefficient differs between oxygenated hemoglobin and deoxygenated hemoglobin, and second illumination light in a wavelength band different from that of the first illumination light. Sequentially applying the first and second illumination light to the internal body portion allows obtainment of an oxygen saturation level of blood. According to this technique, a hypoxic area being a cancer symptom is indicated by artificial color, so it is possible to find out cancer at sight.

To accurately find out cancer, a normal video image obtained in the normal observation and two types of special video images, that is, a vessel pattern video image and an oxygen saturation video image obtained in the special observation are preferably displayed together in a single monitor. Simultaneously displaying the plurality of types of video images, as described above, facilitates making a diagnosis from various viewpoints, and hence greatly improving diagnostic accuracy. Note that, Japanese Patent Laid-Open Publication No. 2003-033324 discloses simultaneous display of a plurality of types of video images in detail.

As described above, the normal video image, the vessel pattern video image, and the oxygen saturation video image are produced using the plurality of types of illumination light in the wavelength bands different from one another. Thus, in order to obtain and display the plurality of types of video images at the same time, lighting is sequentially switched to take out the illumination light required for producing each video image, and imaging is performed in synchronization with the switching of lighting. The amount of illumination light required for appropriate exposure differs from one video image to another, so it is necessary to perform exposure control in accordance with each video image. In general, the exposure control is performed based on the brightness of an immediately preceding frame image. However, in the case of switching and applying the plurality of types of illumination light in a sequential manner, the type of image to be subjected to the exposure control is different from the type of immediately preceding frame image. Therefore, the exposure control cannot be performed appropriately.

SUMMARY OF THE INVENTION

An object of the present invention is to provide an endoscope system that obtains and displays a plurality of types of video images in a sequential manner and performs appropriate exposure control in accordance with the type of each video image, a processor device of the endoscope system, and a method therefor.

To achieve the above and other objects of the present invention, an endoscope system according to the present invention includes a lighting section, an image sensor, a video image processing unit, a brightness detector, an exposure condition determiner, and an exposure controller. The lighting section sequentially and repeatedly applies a plurality of types of illumination light having different wavelength bands to an internal body portion. The image sensor sequentially captures reflected light from the internal body portion, and produces a plurality of types of frame images corresponding to the types of illumination light. The video image processing unit produces a plurality of types of video images based on the plurality of types of frame images. The brightness detector detects the brightness of a specific type of frame image out of the plurality of types of frame images. The exposure condition determiner determines based on the detected brightness, exposure conditions of the plurality of types of frame images to be obtained. The exposure controller regulates exposure of the image sensor in accordance with the determined exposure conditions.

The exposure condition determiner preferably includes a memory and a calculator. The memory stores correlation in the exposure conditions among all types of the frame images. The calculator calculates the exposure condition of each frame image based on the brightness of the specific type of frame image and the correlation.

The correlation in the exposure conditions may be a light intensity ratio among the plurality of types of illumination light, or an exposure time ratio of the image sensor to obtain each of the plurality of types of frame images.

The memory preferably stores first correlation for making the visibility of a specific video image produced from the specific type of frame images higher than that of the other video images, and second correlation for making the visibility of two or more of the video images including the specific video image higher than that of the other video images. One of the first and second correlation is preferably chosen manually.

The plurality of types of video images produced with use of the first or second correlation may have different brightness or different frame rates from each other.

The plurality of types of video images may include a normal video image obtained under white light, an oxygen saturation video image that images an oxygen saturation level of blood, and a vessel pattern video image that images a blood vessel pattern of specific depth.

The lighting section may include a plurality of semiconductor light sources for emitting the plurality of types of illumination light. Alternatively, the lighting section may include a broadband light source for emitting broadband light, and a wavelength splitter for splitting light in a specific wavelength band from the broadband light to produce the plurality of types of illumination light.

A processor device of an endoscope system according to the present invention includes a video image processing unit, a brightness detector, an exposure condition determiner, and an exposure controller. The video image processing unit produces a plurality of types of video images based on a plurality of types of frame images. The brightness detector detects the brightness of a specific type of frame image out of the plurality of types of frame images. The exposure condition determiner determines based on the detected brightness, exposure conditions of the plurality of types of frame images to be obtained. The exposure controller regulates exposure of the image sensor in accordance with the determined exposure conditions.

An exposure control method of an endoscope system includes the steps of sequentially and repeatedly applying a plurality of types of illumination light having different wavelength bands to an internal body portion; sequentially capturing reflected light from the internal body portion, and producing a plurality of types of frame images corresponding to the types of illumination light; producing a plurality of types of video images based on the plurality of types of frame images; detecting brightness of a specific type of frame image out of the plurality of types of frame images; determining based on the detected brightness, exposure conditions of the plurality of types of frame images to be obtained; and regulating exposure of the image sensor in accordance with the determined exposure conditions.

According to the present invention, the exposure conditions are determined in accordance with the types of video images, based on the brightness of the specific video image to which a user gives the greatest attention out of the plurality of types of video images. Exposure is controlled based on the determined exposure conditions. Therefore, not only the specific video image but also the other video images have appropriate exposure. The determination of the exposure conditions is easily performed by measurement of the brightness of the specific video image.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 3A is a graph showing emission spectrum of normal light;

FIG. 3B shows graphs that represent emission spectra of first and second measurement light, the normal light, and pattern detection light;

FIG. 6 is an explanatory view of a method for calculating light intensity in each of an oxygen saturation frame period, a normal frame period, and a vessel pattern frame period;

FIG. 7 is a table showing a light intensity ratio among frames;

FIG. 9 is an explanatory view of a method for calculating exposure time in each of the oxygen saturation frame period, the normal frame period, and the vessel pattern frame period;

FIG. 10 is a table showing an exposure time ratio among frames;

DESCRIPTION OF THE PREFERRED EMBODIMENTS

First Embodiment

Figure 1:
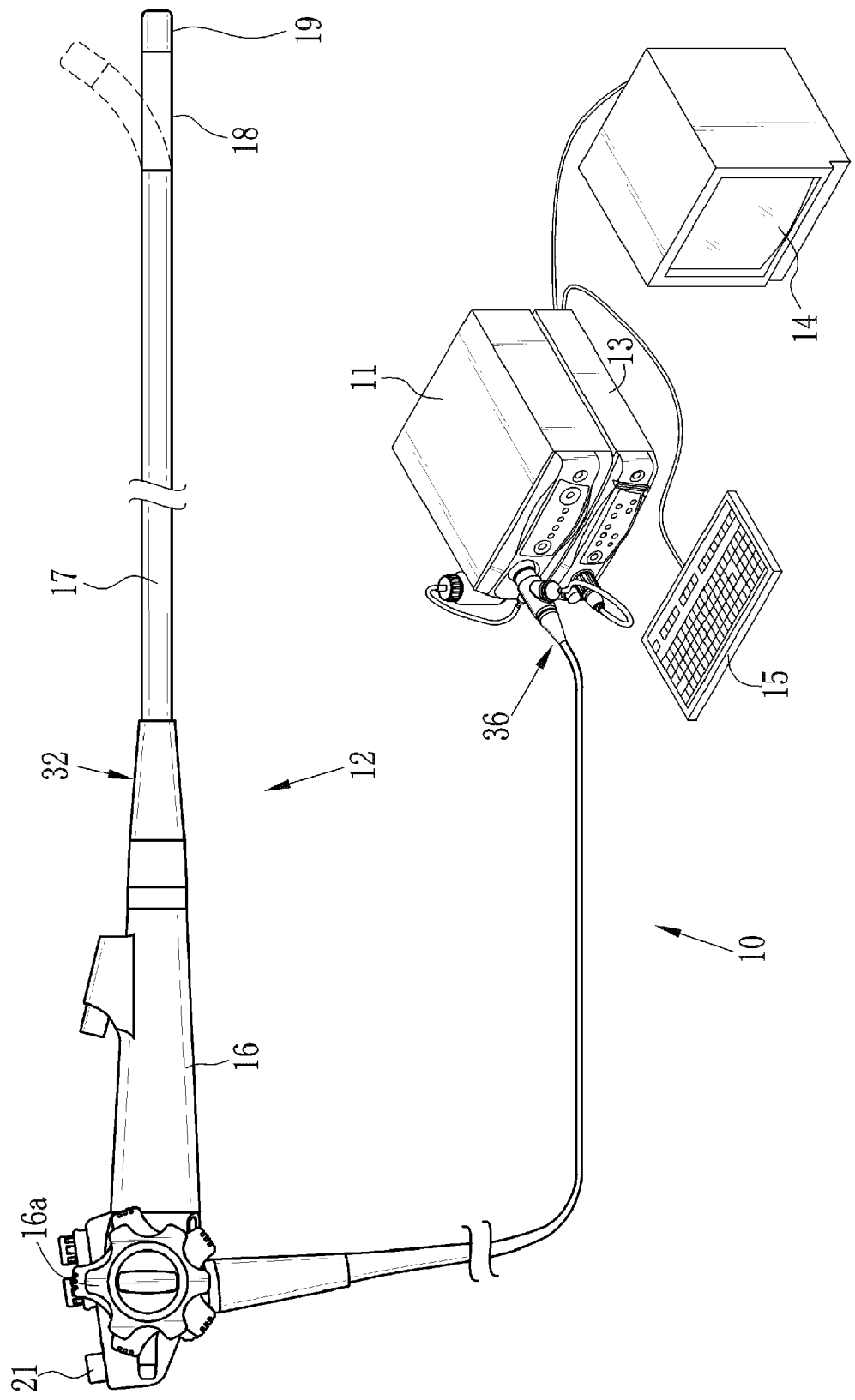
FIG. 1 is a schematic view of an endoscope system.

As shown in FIG. 1, an endoscope system 10 is constituted of a light source device 11, an electronic endoscope 12, a processor device 13, a monitor 14, and an input device 15 such as a keyboard. The light source device 11 produces illumination light for illuminating the interior of a patient's body cavity. The illumination light from the light source device 11 is led through a light guide, and applied to an internal body portion. The electronic endoscope 12 captures the light reflected from the body portion, and outputs an image signal. The processor device 13 applies image processing to the image signal. An endoscopic image obtained by the image processing is displayed on the monitor 14.

The electronic endoscope 12 is provided with a flexible elongated tube 17, a steering assembly 18, and a head assembly 19 provided in this order from the side of a control handle unit 16. The steering assembly 18 is flexibly bent by a turn of an angle knob 16a provided on the control handle unit 16. By bending the steering assembly 18 in an arbitrary direction and angle, the head assembly 19 is aimed at the desired internal body portion to be examined.

The endoscope system 10 has a normal observation mode in which a normal video image in the visible light range from blue to red is displayed on the monitor 14, and a special observation mode in which three types of video images i.e. the normal video image, a vessel pattern video image that emphasizes a blood vessel in specific depth, and an oxygen saturation video image that images an oxygen saturation level of blood are displayed at the same time on the monitor 14.

The special observation mode includes three sub-modes, that is, a key video image preference mode for improving the visibility of a specific single video image out of the three types of video images, a two video image preference mode for improving the visibility of two video images out of the three types of video images, and a three video image preference mode for improving the visibility of all the three types of video images. Any one of the three preference modes is chosen in the special observation mode. The switching between the normal observation mode and the special observation mode and the switching among the three preference modes are performed manually by operation of a mode switch 21 of the electronic endoscope 12, or automatically based on input data from the input device 15.

Figure 2:
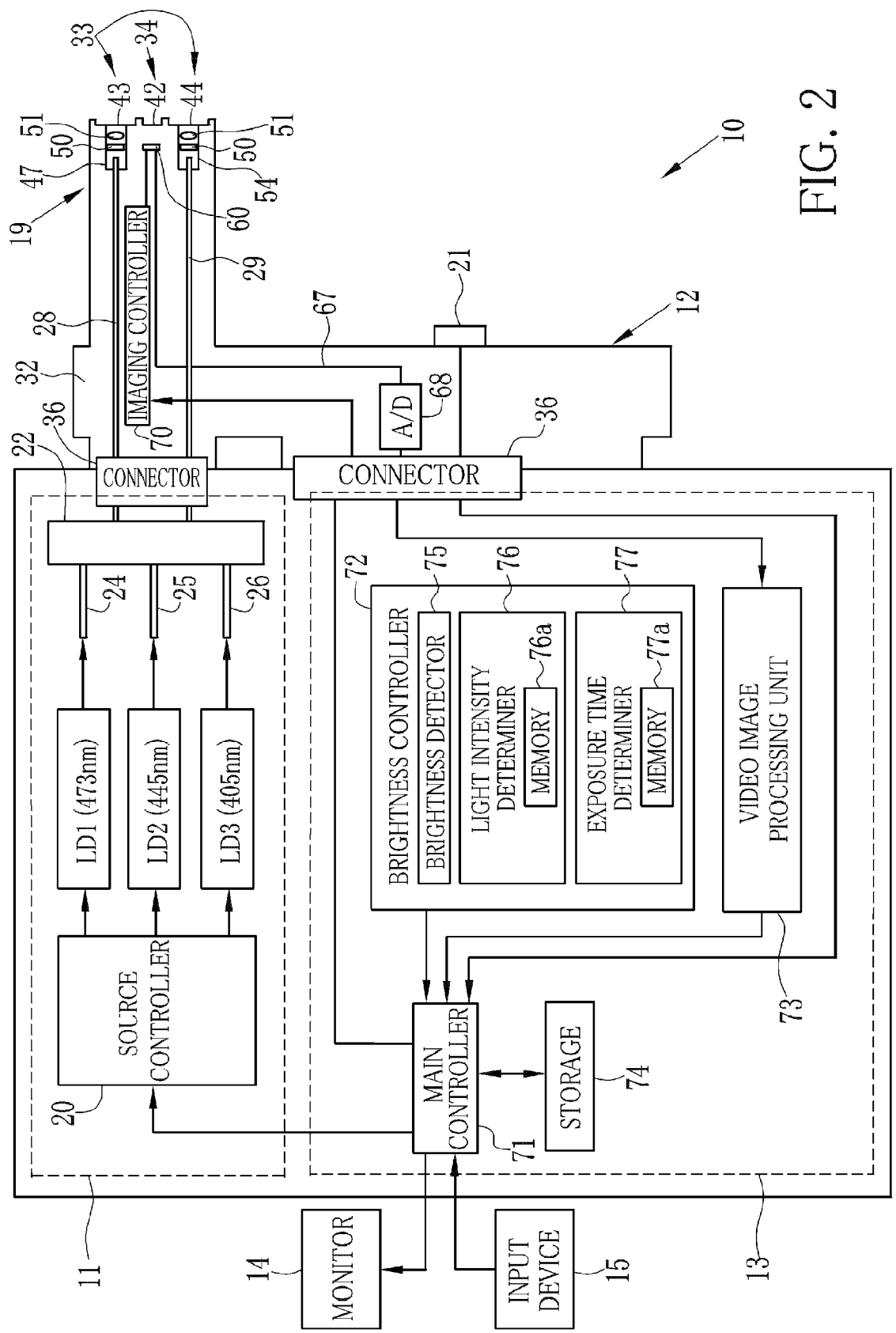
FIG. 2 is a block diagram of an endoscope system according to a first embodiment.

As shown in FIG. 2, the light source device 11 includes three laser sources LD1, LD2, and LD3 and a source controller 20. The laser source LD1 emits a first laser beam having a center wavelength of 473 nm. Most of the first laser beam excites a phosphor 50 disposed in the head assembly 19 of the electronic endoscope 12, and the excited phosphor 50 produces fluorescence in a wavelength range from green to red. The remains of the first laser beam passes through the phosphor 50. The laser source LD2 emits a second laser beam having a center wavelength of 445 nm. Most of the second laser beam excites the phosphor 50, so the excited phosphor 50 produces fluorescence in a wavelength range from green to red. The remains of the second laser beam passes through the phosphor 50. The laser source LD3 emits a third laser beam having a center wavelength of 405 nm. Although most of the third laser beam passes through the phosphor 50, a part of the third laser beam excites the phosphor 50 and the excited phosphor 50 produces fluorescence in a wavelength range from green to red. The first to third laser beams emitted from the laser sources LD1 to LD3 enter optical fibers 24 to 26 through condenser lenses (not shown), respectively.

Note that, the first laser beam is preferably in a wavelength range of 460 to 480 nm. The second laser beam is preferably in a wavelength range of 440 to 460 nm. The third laser beam is preferably in a wavelength range of 400 to 410 nm. As the laser source LD1, LD2, or LD3, a broad-area type InGaN laser diode, InGaNAs laser diode, GaNAs laser diode, or the like is available.

The source controller 20 controls emission timing of each of the laser sources LD1, LD2, and LD3. In this embodiment, as shown in FIG. 3A, in the normal observation mode, the laser source LD2 is turned on, while the other laser sources LD1 and LD3 are turned off. The entrance of the second laser beam from the laser source LD2 into the phosphor 50 produces white light (pseudo white light) by mixing of the fluorescence emitted from the phosphor 50 and the second laser beam passed through the phosphor 50 without being absorbed. This white light is applied to the internal body portion as normal light.

Figure 5A:
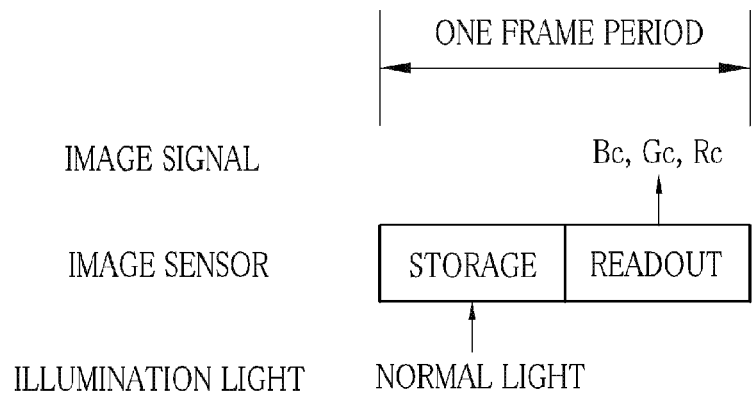
FIG. 5A is an explanatory view of the operation of the image sensor in a normal observation mode of the first embodiment.
Figure 5B:
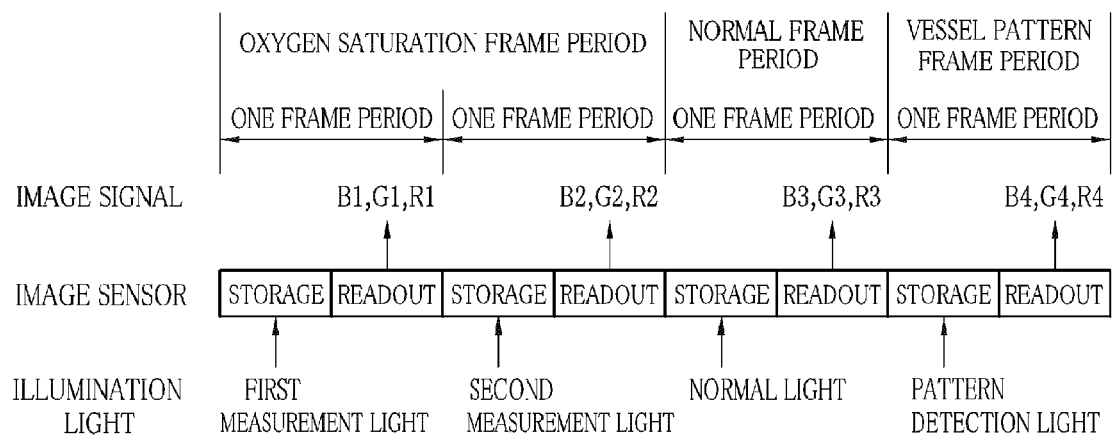
FIG. 5B is an explanatory view of the operation of the image sensor in a special observation mode of the first embodiment.

In the special observation mode, on the other hand, an oxygen saturation frame image for producing an oxygen saturation video image, a normal frame image for producing a normal video image, and a vessel pattern frame image for producing a vessel pattern video image are obtained in a sequential manner (see FIG. 5B). The laser sources LD1 to LD3 are turned on and off at different timing in each frame.

As shown in FIG. 3B, in a first frame period of an oxygen saturation frame period, the laser source LD1 is turned on, while the other laser sources LD2 and LD3 are turned off. In a second frame period of the oxygen saturation frame period, the laser source LD2 is turned on, while the other laser sources LD1 and LD3 are turned off. Thus, in the first frame period, first measurement light, which includes the first laser beam from the laser source LD1 and the fluorescence produced by the phosphor 50 excited by the first laser beam, is applied to the internal body portion. In the second frame period, second measurement light, which includes the second laser beam emitted from the laser source LD2 and the fluorescence produced by the phosphor 50 excited by the second laser beam, is applied to the internal body portion. The measurement light may be applied only during charge storage time, instead of the entire frame period.

In a normal frame period, as in the case of the normal observation mode, the normal light, which includes the second laser beam emitted from the laser source LD2 and the fluorescence produced by the phosphor 50 excited by the second laser beam, is applied to the internal body portion. In a vessel pattern frame period, the laser sources LD2 and LD3 are turned on, while the other laser source LD1 is turned off. Thus, pattern detection light, which includes the second laser beam emitted from the laser source LD2, the third laser beam emitted from the laser source LD3, and the fluorescence produced by the phosphor 50 excited by the second and third laser beams, is applied to the internal body portion.

The source controller 20 regulates the light intensity P of the first and second measurement light, the light intensity Q of the normal light, and the light intensity R of the pattern detection light under the direction of a brightness controller 72 of the processor device 13.

A coupler 22 branches the first to third laser beams transmitted through the optical fibers 24 to 26 in two beams. The branched two beams are transmitted through light guides 28 and 29, respectively. Each of the light guides 28 and 29 is made of a bundle of a number of optical fibers.

The electronic endoscope 12 is provided with a lighting section 33 for applying the two beams transmitted through the light guides 28 and 29 to the internal body portion, and an image pickup section 34 for imaging the internal body portion. The electronic endoscope 12 is provided with a connector 36 through which the electronic endoscope 12 is detachably connected to the light source device 11 and the processor device 13.

The lighting section 33 includes two lighting windows 43 and 44 disposed on both sides of the image pickup section 34, and light projection units 47 and 54 disposed in the recess of the lighting windows 43 and 44, respectively. Each of the light projection units 47 and 54 contains the phosphor 50 and a lens 51. In each of the light projection units 47 and 54, the laser beam transmitted through the light guide 28, 29 enters the phosphor 50 to produce the fluorescence. This fluorescence and the laser beam passed through the phosphor 50 are applied to the internal body portion through the lens 51 and the lighting window 43, 44. The image pickup section 34 includes an imaging window 42 positioned approximately at the center of the head assembly 19 and an image sensor 60 disposed in the recess of the imaging window 42.

The phosphor 50 is made of a plurality of types of fluorescent substances (for example, YAG-based fluorescent substance or BAM ($BaMgAl_{10}O_{17}$)-based fluorescent substance) that absorb a part of the first to third laser beams and emit the green to red fluorescence. The entrance of each of the first to third laser beams into the phosphor 50 produces white light (pseudo white light) by mixing of the green to red fluorescence produced by the phosphor 50 and each of the first to third laser beams passed through the phosphor 50 without being absorbed.

The phosphor 50 preferably has an approximately rectangular parallelepiped shape. The phosphor 50 may be formed by compacting the fluorescent substances by a binder into the rectangular parallelepiped shape. The mixture of resin such as inorganic glass and the fluorescent substance may be formed into the rectangular parallelepiped shape. This phosphor 50 is known under the trademark of Micro White (MW).

In the recess of the imaging window 42, an optical system such as an objective lens unit (not shown) is provided to capture image light of the internal body portion. In the recess of the objective lens unit, the image sensor 60 such as a CCD (charge coupled device) image sensor is provided to perform photoelectric conversion of the captured image light. Note that, a IT (interline transfer) type color CCD image sensor is used as the image sensor 60, but a color CMOS (complementary metal-oxide semiconductor) image sensor having a global shutter function may be used instead.

Figure 4A:
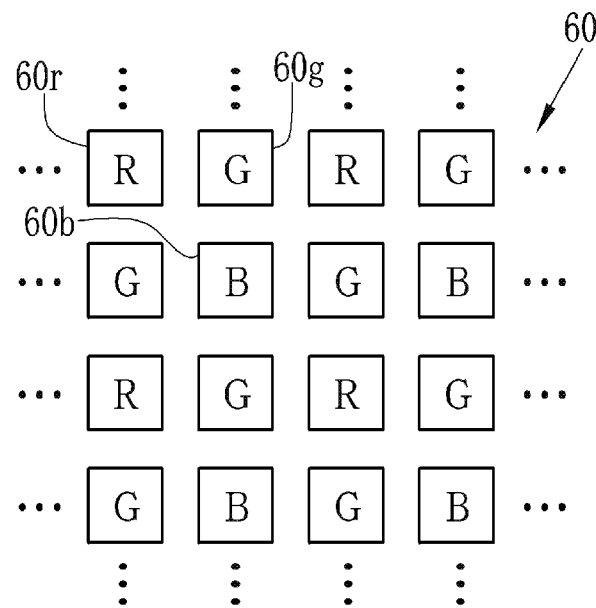
FIG. 4A is an explanatory view of an arrangement of B, G, and R pixels in a color image sensor.
Figure 4B:
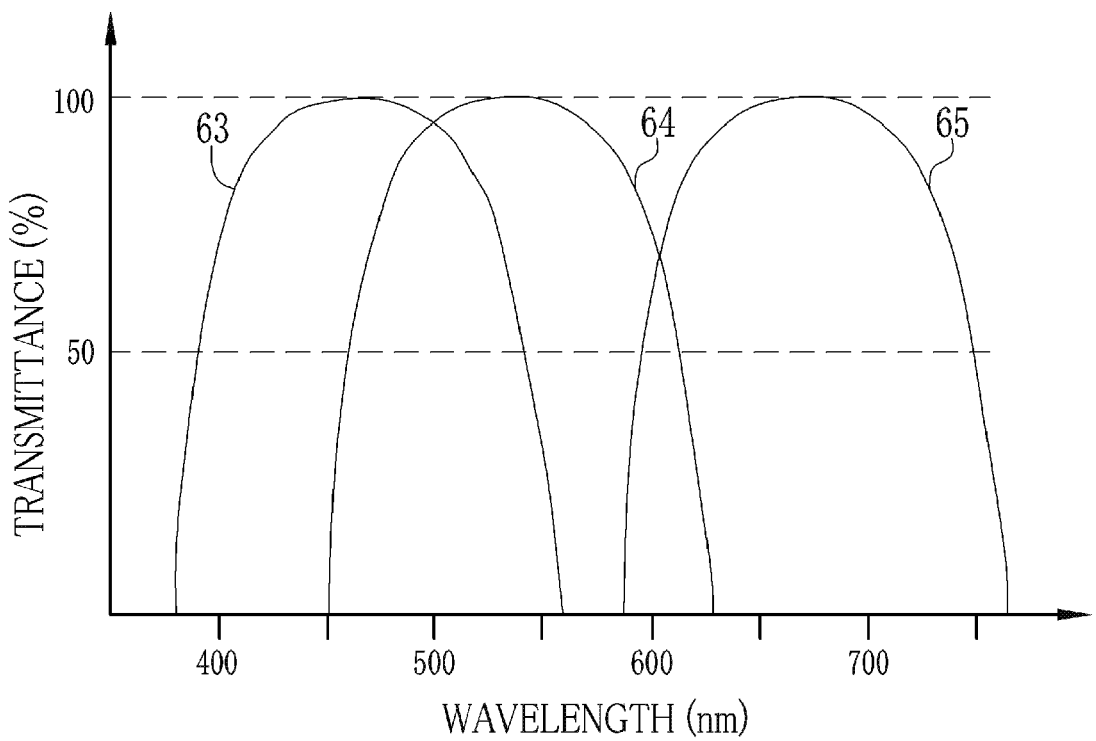
FIG. 4B is a graph showing spectral transmittance of the B, G, and R pixels.

The image sensor 60 receives the image light from the objective lens unit at its light receiving surface (imaging surface), and performs the photoelectric conversion of the received image light to output an analog image signal. As shown in FIG. 4A, the image sensor 60 has arrangement patterns of 2-by 2-pixel arranged in horizontal and vertical directions in its light receiving surface. Each arrangement pattern includes one B pixel 60b having a B (blue) color filter, two G pixels 60g having a G (green) color filter, and one R pixel 60r having a R (red) color filter. The B, G, and R color filters have high spectral transmittance in a blue wavelength range, a green wavelength range, and a red wavelength range, as represented by curves 63, 64, and 65 of FIG. 4B, respectively.

Figure 4C:
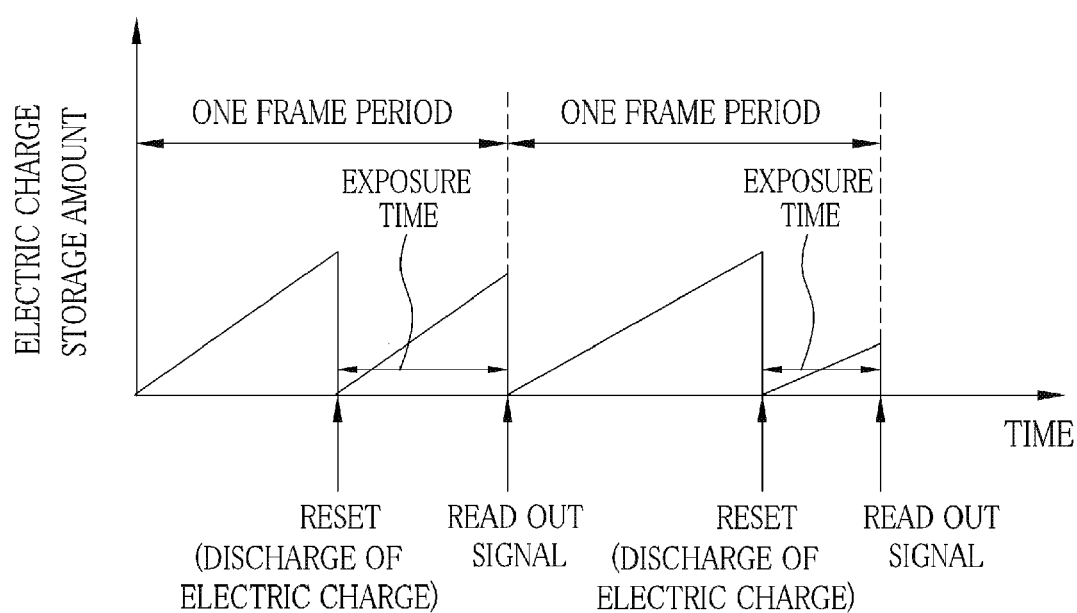
FIG. 4C is a graph for explaining the operation of an electronic shutter.

The image sensor 60 has an electronic shutter function for regulating the charge storage time. By the electronic shutter function, as shown in FIG. 4C, pixels are reset (stored electric charge is discharged) at predetermined timing in one frame period. After the reset, stored electric charge is read out as an image signal. The charge storage time after the reset corresponds to exposure time.

The analog image signal outputted from the image sensor 60 is inputted to an A/D converter 68 through a cable 67. The A/D converter 68 converts the image signal into a digital image signal in accordance with its voltage level. The converted image signal is inputted to the processor device 13 through the connector 36.

An imaging controller 70 controls the image sensor 60. As shown in FIG. 5A, in the normal observation mode, a storage step and a readout step are performed within one frame period. In the storage step, electric charge produced in each pixel by irradiation with the normal light is stored. In the readout step, the stored electric charge is read out as a blue signal Bc, a green signal Gc, and a red signal Rc. The storage step and the readout step are repeated, while the endoscope system 10 is in the normal observation mode.

In the special observation mode, on the other hand, as shown in FIG. 5B, a storage step and a readout step are performed in the first frame period of the oxygen saturation frame period. In the storage step, electric charge produced in each pixel by irradiation with the first measurement light (first laser beam (473 nm)+fluorescence) is stored. In the readout step, the stored electric charge is read out as a blue signal B1, a green signal G1, and a red signal R1. After that, in the second frame period, a storage step for storing electric charge produced by irradiation with the second measurement light (second laser beam (445 nm)+fluorescence) and a readout step for reading out the stored electric charge as a blue signal B2, a green signal G2, and a red signal R2 are performed.

In the next normal frame period, a storage step for storing electric charge produced by irradiation with the normal light and a readout step for reading out the stored electric charge as a blue signal B3, a green signal G3, and a red signal R3 are performed. In the next vessel pattern frame period, a storage step for storing electric charge produced by irradiation with the pattern detection light and a readout step for reading out the stored electric charge as a blue signal B4, a green signal G4, and a red signal R4 are performed. Four frame images that are produced in the four frame periods compose a frame image set. The production of the frame image set is repeated, while the endoscope system 10 is in the special observation mode.

The processor device 13 is constituted of a main controller 71, a brightness controller 72, a video image processing unit 73, and storage 74. The main controller 71 is connected to the monitor 14 and the input device 15. The main controller 71 controls the operation of the video image processing unit 73, the source controller 20 of the light source device 11, the imaging controller 70 of the electronic endoscope 12, and the monitor 14 based on input from the mode switch 21 of the electronic endoscope 12 and the input device 15.

In the special observation mode, the brightness controller 72 controls the brightness of all the three types of video images based on a key video image chosen from the three types of video images. The brightness controller 72 includes a brightness detector 75, a light intensity determiner 76, and an exposure time determiner 77. The brightness detector 75 detects the brightness Y of an entire latest frame image of the key video image. The brightness may be, for example, an average of pixel values of all the pixels in the latest frame image or another index.

As shown in FIG. 6, the light intensity determiner 76 determines the light intensity (reference light intensity) P of the first and second measurement light to obtain the next frame image set, based on the brightness Y of the latest frame image of the key video image detected by the brightness detector 75. Then, the light intensity Q of the normal light and the light intensity R of the pattern detection light are calculated based on the light intensity P of the first and second measurement light and a light intensity ratio (La:Lb:Lc=the light intensity to be applied in the oxygen saturation frame period:that in the normal frame period:that in the vessel pattern frame period) among frames that is stored in advance in a memory 76a as a fixed value. The light intensity Q of the normal light is obtained by multiplying the light intensity P by a modification ratio of Lb/La. The light intensity R of the pattern detection light is obtained by multiplying the light intensity P by a modification ratio of Lc/La. The first and second measurement light, the normal light, and the pattern detection light are produced so as to have the light intensity of P, Q, and R, respectively.

Figure 8A:
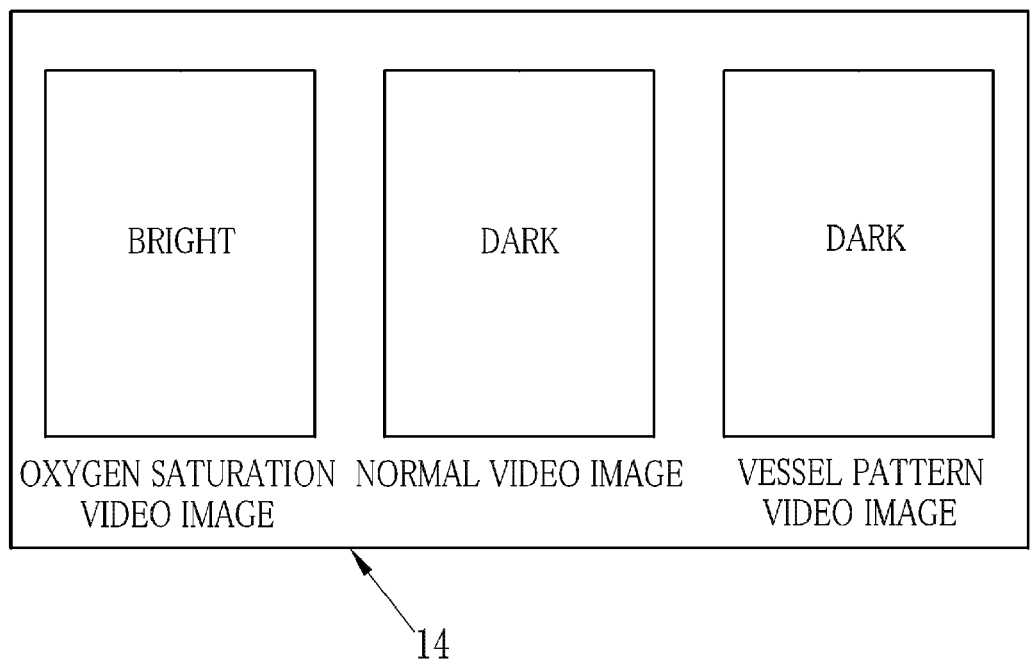
FIG. 8A is a plan view of a monitor in which a key video image is displayed more brightly than the other video images.

As shown in FIG. 7, the light intensity ratio among frames is different depending on each of the three modes, that is, the key video image preference mode, the two vide image preference mode, and the three video image preference mode. In the case of the key video image preference mode, the light intensity ratio is determined such that the brightness of the key video image is higher than that of the other video images. When the oxygen saturation video image is designated as the key video image, for example, the light intensity ratio satisfies La>Lb and La>Lc. In this case, as shown in FIG. 8A, the oxygen saturation video image is displayed on the monitor 14 more brightly than the normal video image and the vessel pattern video image.

Figure 8B:
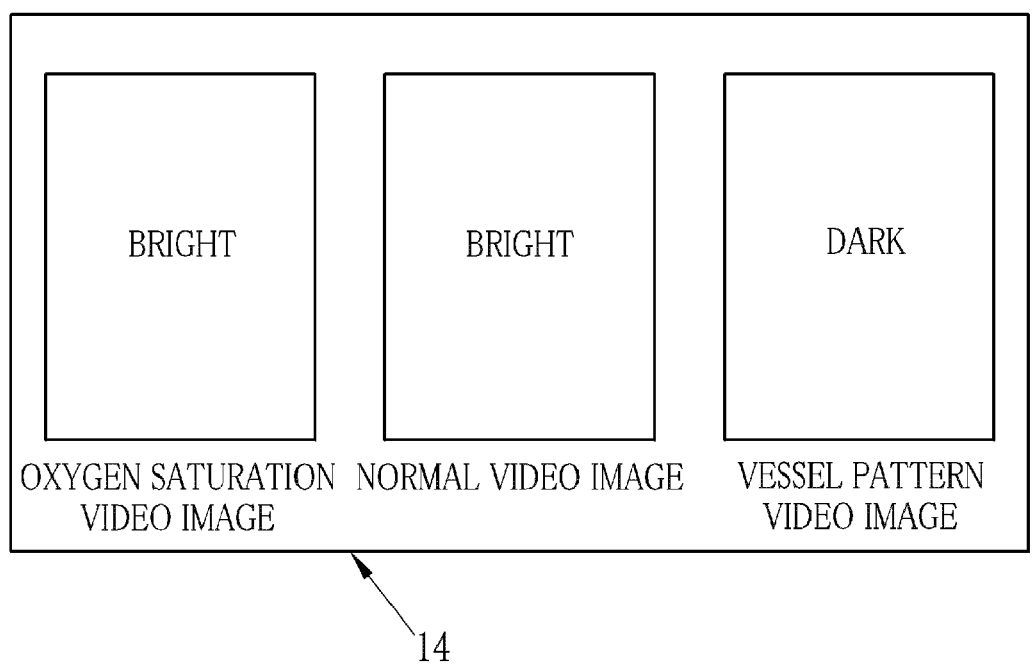
FIG. 8B is a plan view of the monitor in which two video images including the key video image are displayed more brightly than the other video image.

In the case of the two video image preference mode, the light intensity ratio is determined such that the brightness of the two video images including the key video image is higher than that of the other image. Taking a case of improving the visibility of the oxygen saturation video image and the normal video image as an example, the light intensity ratio satisfies La>Lc and Lb>Lc. In this case, as shown in FIG. 8B, the oxygen saturation video image and the normal video image are displayed on the monitor 14 more brightly than the vessel pattern video image. In the case of the three video image preference mode, the light intensity ratio is determined such that the brightness of all the video images is the same. The light intensity ratio satisfies La=Lb=Lc. The light intensity ratios are obtained by experiments.

As shown in FIG. 9, the exposure time determiner 77 determines the exposure time (reference exposure time) K of the image sensor 60 to obtain the next frame image set, based on the brightness Y of the latest frame image of the key video image detected by the brightness detector 75. Then, the exposure time L of the image sensor 60 in the normal frame period and the exposure time M thereof in the vessel pattern frame period are calculated based on the exposure time K and an exposure time ratio (Ea:Eb:Ec=the exposure time to be applied in the oxygen saturation frame period:that in the normal frame period:that in the vessel pattern frame period) among frames that is stored in advance in a memory 77a as a fixed value. The exposure time L in the normal frame period is obtained by multiplying the exposure time K by a modification ratio of Eb/Ea. The exposure time M in the vessel pattern frame period is obtained by multiplying the exposure time K by a modification ratio of Ec/Ea. The imaging controller 70 of the electronic endoscope 12 controls the readout timing of the image sensor 60 based on the exposure time K, L, and M.

As shown in FIG. 10, the exposure time ratio among frames is different depending on each of the three modes, that is, the key video image preference mode, the two vide image preference mode, and the three video image preference mode. In the case of the key video image preference mode, the exposure time ratio is determined such that the brightness of the key video image is higher than that of the other video images. When the oxygen saturation video image is designated as the key video image, for example, the exposure time ratio satisfies Ea>Eb and Ea>Ec. In this case, as shown in FIG. 8A, the oxygen saturation video image is displayed on the monitor 14 more brightly than the normal video image and the vessel pattern video image.

In the case of the two video image preference mode, the exposure time ratio is determined such that the brightness of the two video images including the key video image is higher than that of the other image. Taking a case of improving the visibility of the oxygen saturation video image and the normal video image as an example, the exposure time ratio satisfies Ea>Ec and Eb>Ec. In this case, as shown in FIG. 8B, the oxygen saturation video image and the normal video image are displayed on the monitor 14 more brightly than the vessel pattern video image. In the case of the three video image preference mode, the exposure time ratio is determined such that the brightness of all the video images is the same. The exposure time ratio satisfies Ea=Eb=Ec.

Figure 11:
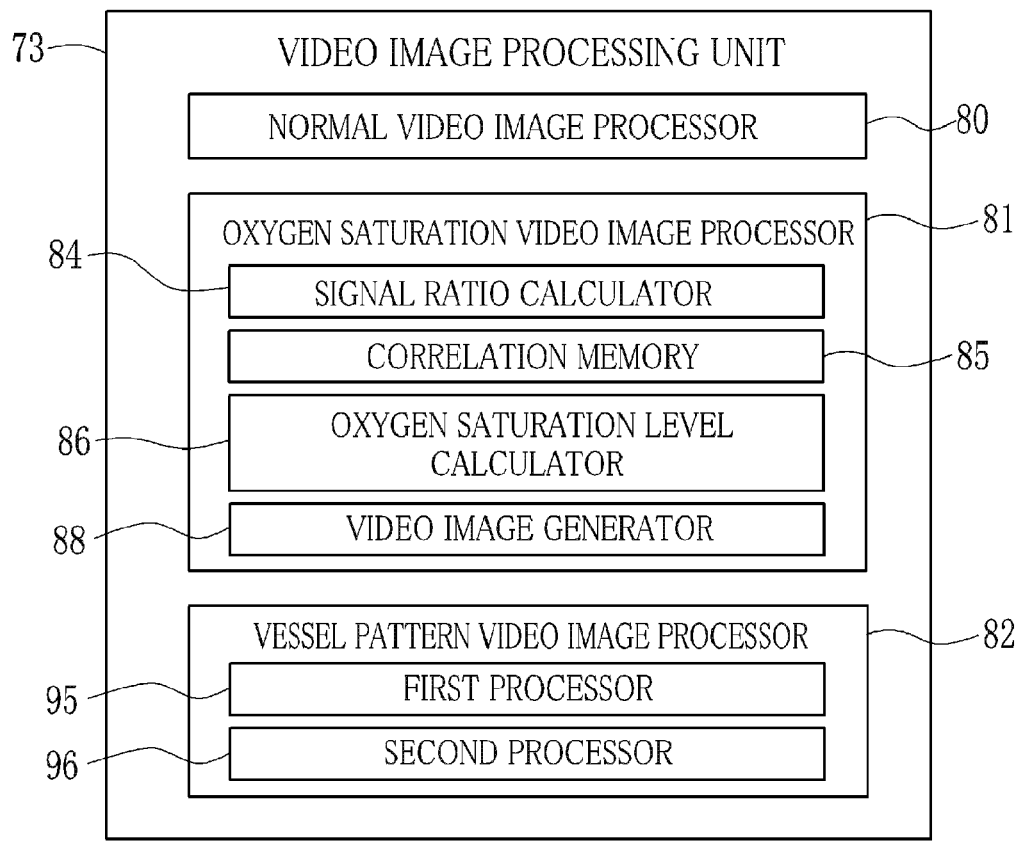
FIG. 11 is a block diagram of a video image processing unit.

As shown in FIG. 11, the video image processing unit 73 includes a normal video image processor 80, an oxygen saturation video image processor 81, and a vessel pattern video image processor 82. In the normal observation mode, the normal video image processor 80 applies predetermined image processing to the image signals Bc, Gc, and Rc sent from the electronic endoscope 12 to produces a normal image. The produced normal images are sequentially outputted, so the normal video image is displayed on the monitor 14. In the special observation mode, on the other hand, the normal video image processor 80 applies the predetermined image processing to the image signals B3, G3, and R3 to produces the normal video image.

The oxygen saturation video image processor 81 calculates the oxygen saturation level of blood based on the image signals inputted from the electronic endoscope 12, and produces an oxygen saturation image in which the oxygen saturation level is reflected. The produced oxygen saturation images are sequentially outputted, so the oxygen saturation video image is displayed on the monitor 14. The calculation of the oxygen saturation level uses the blue signal B1 of a first frame image and the green signal G2 and the red signal R2 of a second frame image obtained in the oxygen saturation frame period.

The oxygen saturation video image processor 81 includes a signal ratio calculator 84, a correlation memory 85, an oxygen saturation level calculator 86, and a video image generator 88. The signal ratio calculator 84 calculates a signal ratio B1/G2 between the blue signal B1 of the first frame image and the green signal G2 of the second frame image, and a signal ratio R2/G2 between the red signal R2 and the green signal G2 of the second frame image. The signal ratio calculator 84 calculates the signal ratios with respect to the pixel situated in the same position. The signal ratios may be calculated with respect to each and every pixel, or only in pixels situated within a blood vessel area. In this case, the blood vessel area is determined based on difference in the image signal between the blood vessel area and the other area.

Figure 12:
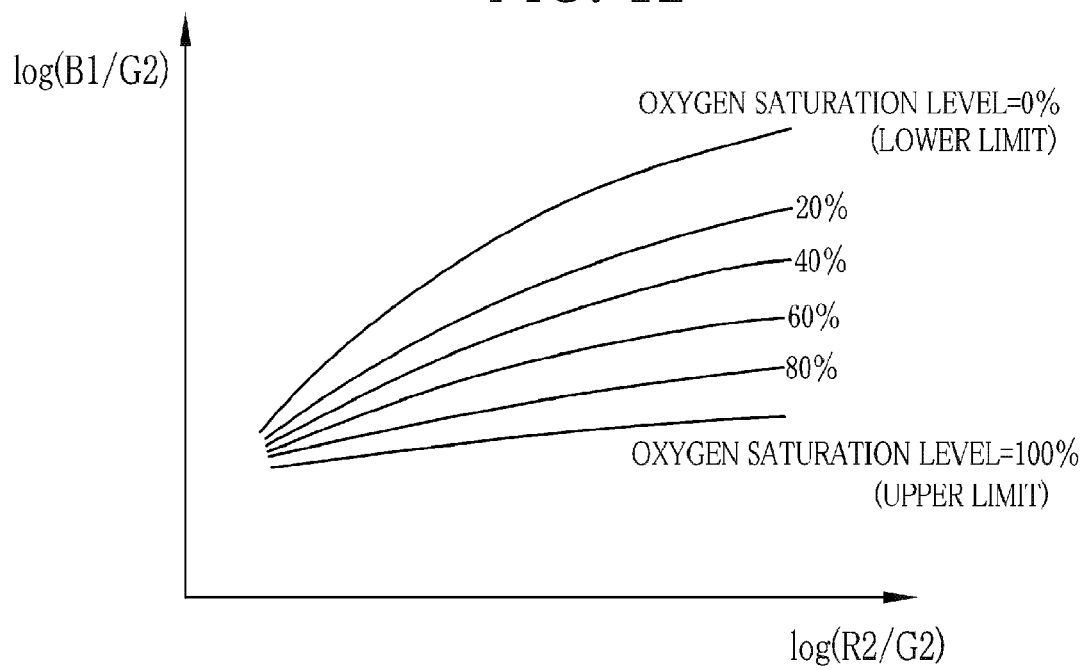
FIG. 12 is a graph showing the correlation between an oxygen saturation level and signal ratios B1/G2 and R2/G2.

The correlation memory 85 stores the correlation among the signal ratios B1/G2 and R2/G2 and the oxygen saturation level. As shown in FIG. 12, this correlation takes the form of a two-dimensional table in which contour lines representing the oxygen saturation level are defined in two-dimensional space. The position and shape of the contour lines are obtained by physical simulation of light scattering, and are variable in accordance with blood volume. For example, variation in the blood volume widens or narrows distance between the contour lines. Note that, the signal ratios B1/G2 and R2/G2 are depicted in log scale.

Figure 13:
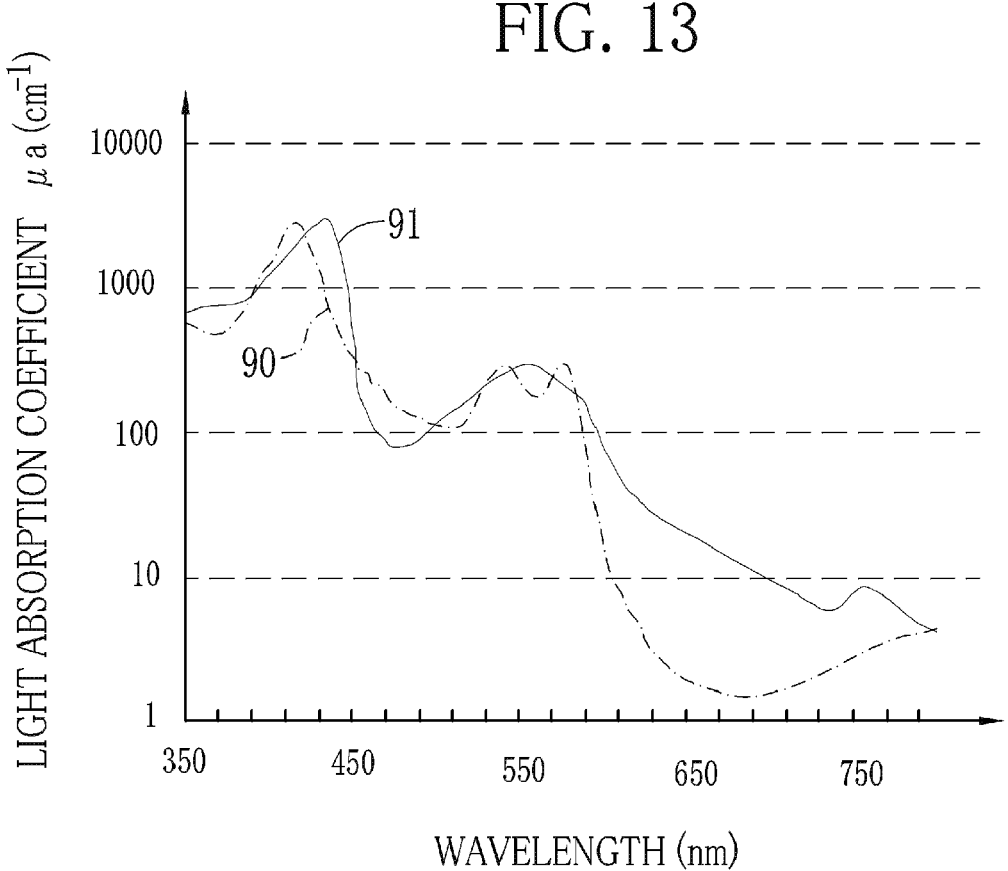
FIG. 13 is a graph showing a light absorption coefficient of hemoglobin.

The correlation is closely related to the light absorbing property and light scattering property of oxygenated hemoglobin and deoxygenated hemoglobin, as shown in FIG. 13. In FIG. 13, a line 90 represents a light absorption coefficient of the oxygenated hemoglobin, and a line 91 represents a light absorption coefficient of the deoxygenated hemoglobin. The use of a wavelength of, for example, 473 nm at which the light absorption coefficient much differs between the oxygenated hemoglobin and the deoxygenated hemoglobin allows the obtainment of the oxygen saturation level. However, the blue signal B1 that corresponds to the light of 473 nm is highly dependent not only on the oxygen saturation level but also on the blood volume. Therefore, the use of the signal ratios B1/G2 and R2/G2, which are obtained from the red signal R2 that is mainly dependent on the blood volume and the green signal G2 being a reference signal (standardization signal) of the blue signal B1 and the red signal R2, in addition to the blue signal B1, allows the obtainment of the oxygen saturation level with high accuracy while eliminating the influence of the blood volume.

Figure 14:
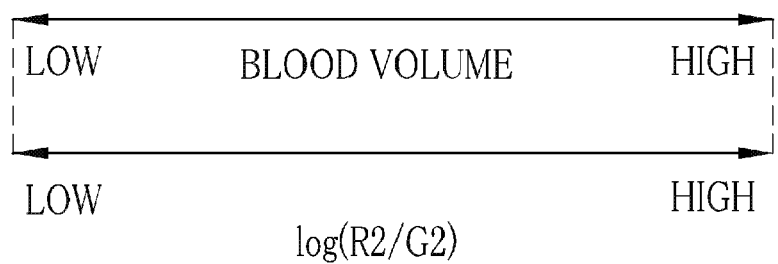
FIG. 14 is a graph showing the correlation between blood volume and the signal ratio R2/G2.

The correlation memory 85 also stores the correlation between the signal ratio R2/G2 and the blood volume as shown in FIG. 14. This correlation takes the form of a one-dimensional table in which the blood volume is increased with increase in the signal ratio R2/G2. The correlation between the signal ratio R2/G2 and the blood volume is used in calculation of the blood volume.

The following three items hold true according to the dependence of the light absorption coefficient of hemoglobin on a wavelength:
(1) In the vicinity of a wavelength of 470 nm (for example, the blue wavelength range having a center wavelength of 470 nm±10 nm), the light absorption coefficient largely varies in accordance with difference in the oxygen saturation level.
(2) In the green wavelength range between 540 and 580 nm, a mean value of the light absorption coefficient is insusceptible to the oxygen saturation level.
(3) In the red wavelength range between 590 and 700 nm, the light absorption coefficient seems to vary largely in accordance with the oxygen saturation level, but in actual fact, is insusceptible to the oxygen saturation level because a value of the light absorption coefficient is very small.

The reason why the signal ratio B1/G2 increases with increase in the signal ratio R2/G2, in other words, why the contour line representing the oxygen saturation level of 0% ascends slantly, as shown in FIG. 12, is as follows. As described above, the blood volume increases with increase in the signal ratio R2/G2, because of the correlation between the signal ratio R2/G2 and the blood volume. Out of the signals B1, G2, and R2, a signal value of the green signal G2 decreases most greatly with increase in the blood volume, and a signal value of the blue signal B1 decreases next greatly. This is because the light absorption coefficient is higher at a wavelength range of 540 to 580 nm included in the green signal G2 than that at a wavelength range of around 470 nm included in the blue signal B1 (see FIG. 13). Thus, as for the signal ratio B1/G2, the signal value of the green signal G2 decreases more greatly than the signal value of the blue signal B1 with increase in the blood volume. In other words, the signal ratio B1/G2 increases with increase in the blood volume.

Figure 15:
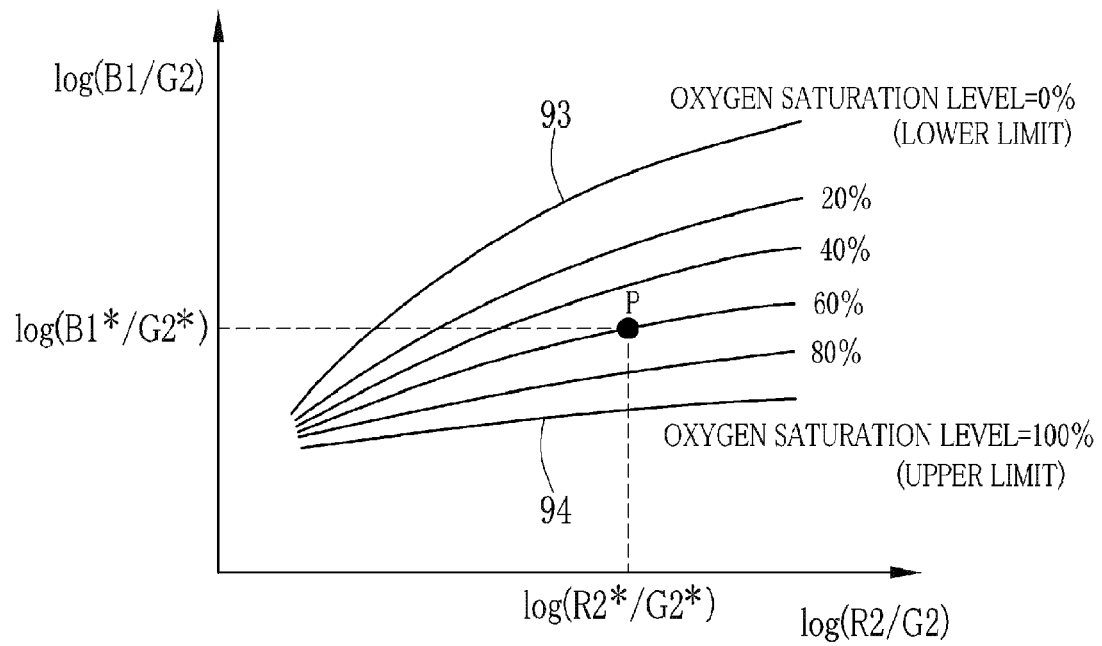
FIG. 15 is an explanatory view of a method for calculating the oxygen saturation level from the signal ratios in the graph of FIG. 12.

The oxygen saturation level calculator 86 calculates the oxygen saturation level of each pixel with the use of the correlations stored in the correlation memory 85 and the signal ratios B1/G2 and R2/G2 obtained by the signal ratio calculator 84. As shown in FIG. 15, a point P that corresponds to the signal ratios B1*/G2* and R2*/G2* obtained by the signal ratio calculator 84 is determined in the correlation stored in the correlation memory 85. When the point P is situated between a lower limit line 93 representing an oxygen saturation level of 0% and an upper limit line 94 representing an oxygen saturation level of 100%, the point P indicates the percentile of the oxygen saturation level. Taking FIG. 15 as an example, the point P is situated in a contour line of 60%, so the oxygen saturation level is 60%.

On the other hand, in a case where the point is out of the range between the lower limit line 93 and the upper limit line 94, if the point is situated above the lower limit line 93, the oxygen saturation level is determined to be 0%. If the point is situated below the upper limit line 94, the oxygen saturation level is determined to be 100%. Note that, in a case where the point is out of the range between the lower limit line 93 and the upper limit line 94, the oxygen saturation level of the pixel is judged to be unreliable and may not be displayed on the monitor 14.

The video image generator 88 produces the oxygen saturation image based on the oxygen saturation level obtained by the oxygen saturation level calculator 86. The oxygen saturation video image is produced from the produced oxygen saturation images. In the oxygen saturation video image, for example, the entire normal video image may be artificially colored with specific colors in accordance with the degree of the oxygen saturation level. In another case, only a hypoxic area, which has the oxygen saturation level lower than a predetermined value, may be artificially colored, while the other areas may be unchanged from the normal video image.

The vessel pattern video image processor 82 includes a first processor 95 and a second processor 96. The first processor 95 produces a first vessel pattern image in which a blood vessel pattern in specific depth such as a superficial blood vessel is emphasized in the normal image. By sequentially outputting the first vessel pattern images, a first vessel pattern video image is displayed on the monitor 14. The second processor 96 produces a second vessel pattern image in which the superficial blood vessel and a medium to deep blood vessel are colored differently. By sequentially outputting the second vessel pattern images, a second vessel pattern video image is displayed on the monitor 14.

In producing the first vessel pattern video image, the light intensity of the second laser beam (445 nm) is set higher than that of the third laser beam (405 nm). In other words, the pattern detection light includes green and red components at a higher rate than a blue component. In producing the second vessel pattern video image, on the other hand, the light intensity of the third laser beam (405 nm) is set higher than that of the second laser beam (445 nm). In other words, the pattern detection light includes the blue component at a higher rate than the green and red components.

Figure 16A:
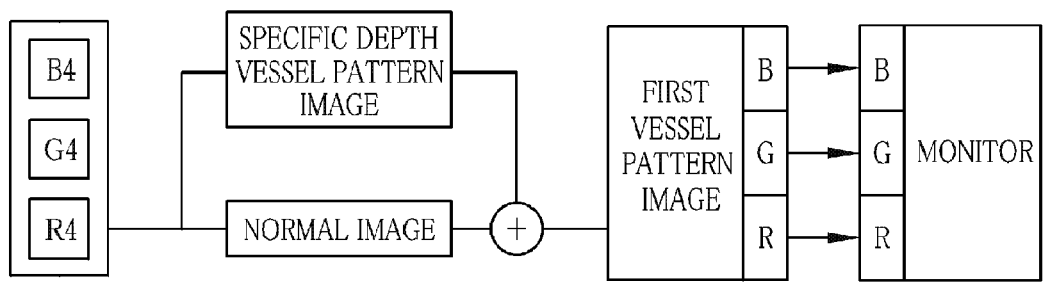
FIG. 16A is an explanatory view of a method for producing a first vessel pattern image.

As shown in FIG. 16A, the first processor 95 produces the normal image and a specific depth vessel pattern image by using the image signals B4, G4, and R4 obtained in the vessel pattern frame period. The image signals B4, G4, and R4 are obtained under illumination light that includes the green and red components at the higher rate than the blue component. Thus, in the production of the normal image, the image signals B4, G4, and R4 are subjected to image processing and converted into values to be obtained under illumination light that includes the blue, green, and red components at an approximately equal rate. The normal image is produced based on the corrected image signals B4, G4, and R4.

In the production of the specific depth vessel pattern image, special image processing is applied to the image signals B4, G4, and R4 to extract and enhance the blood vessels in the specific depth. The produced normal image and the specific depth vessel pattern image are merged to obtain the first vessel pattern image. The B pixels, G pixels, and R pixels of the first vessel pattern image are assigned to B, G, and R channels of the monitor 14, respectively.

Note that, the special image processing includes blood vessel extraction processing using edge enhancement, frequency filtering, and a signal ratio B4/G4. For example, the spatial frequency of an image tends to increase with decrease in the thickness of a blood vessel. Thus, application of high frequency filtering processing allows extraction of a narrow superficial blood vessel. Application of low to medium frequency filtering processing allows extraction of a thick medium to deep blood vessel. Also, since the depth of a blood vessel is directly proportional to the signal ratio B4/G4, a portion having the signal ratio B4/G4 less than a predetermined value can be extracted as the superficial blood vessel. A portion having the signal ratio B4/G4 more than the predetermined value can be extracted as the medium to deep blood vessel.

Figure 16B:
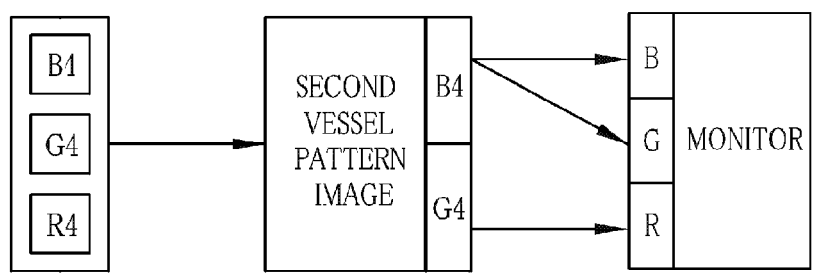
FIG. 16B is an explanatory view of a method for producing a second vessel pattern image.

As shown in FIG. 16B, the second processor 96 produces the second vessel pattern image from the two signals B4 and G4 out of the image signals obtained in the vessel pattern frame period. The signal B4 of the second vessel pattern image is assigned to the B and G channels of the monitor 14, while the signal G4 is assigned to the R channel of the monitor 14. Therefore, the superficial blood vessel and the medium to deep blood vessel are displayed with different colors on the monitor 14. The signals B4 and G4 are obtained under illumination light that includes the blue component at the higher rate than the green and red components, so the superficial blood vessel is enhanced more than the medium to deep blood vessels.

Figure 17A:
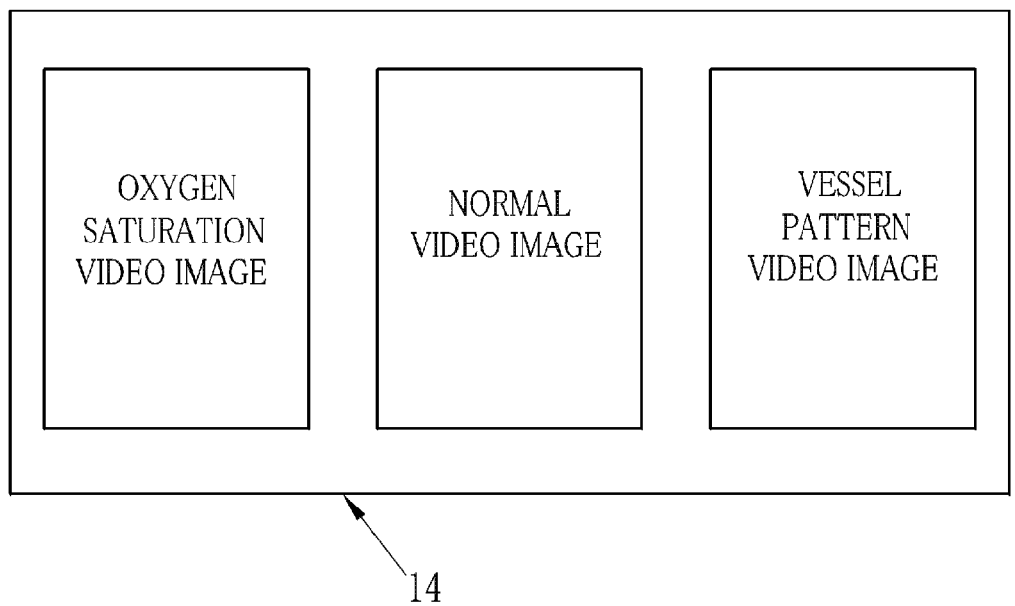
FIG. 17A is a plan view of the monitor in which three types of video images are displayed at the same time.
Figure 17B:
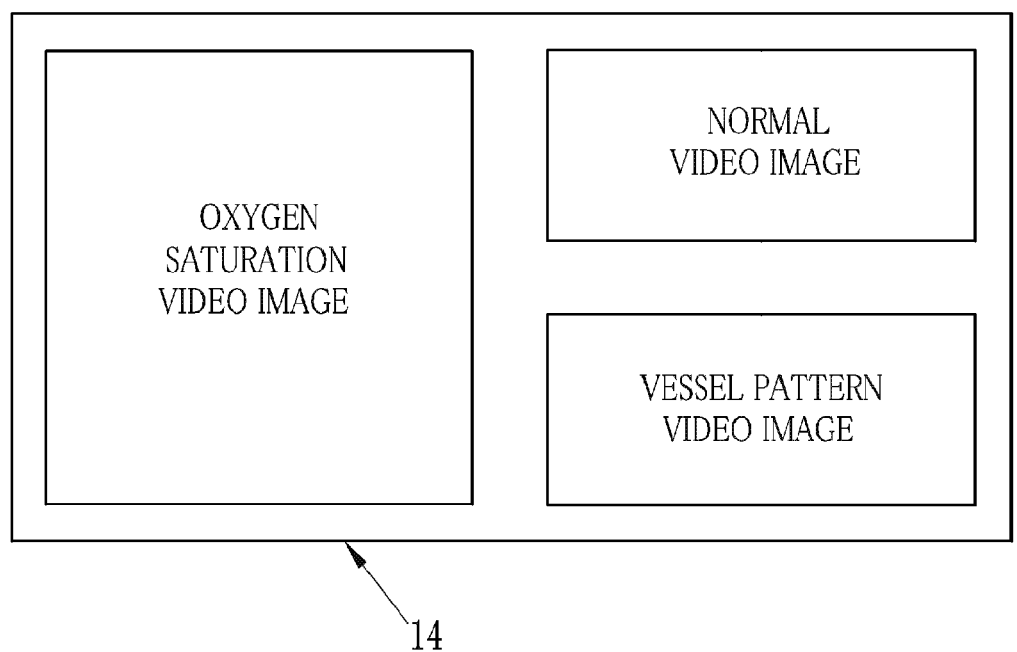
FIG. 17B is a plan view of the monitor in which the three types of video images are displayed at the same time in a way different from that of FIG. 17A.

In the normal observation mode, the main controller 71 displays on the monitor 14 the normal video image that is produced in the video image processing unit 73. In the special observation mode, the main controller 71 displays on the monitor 14 the three video images, i.e. the oxygen saturation video image, the normal video image, and the vessel pattern video image (one or both of the first and second vessel pattern video images) produced in the video image processing unit 73, at the same time. The three video images may be displayed in the same size, as shown in FIG. 17A. Alternatively, as shown in FIG. 17B, the key video image (the oxygen saturation video image in FIG. 17B) may be displayed larger than the other video images (the normal video image and the vessel pattern video image in FIG. 17B) for the purpose of improving the visibility of the key video image. The key video image is set from the input device 15. The key video image may be any image other than the oxygen saturation video image.

Figure 18:
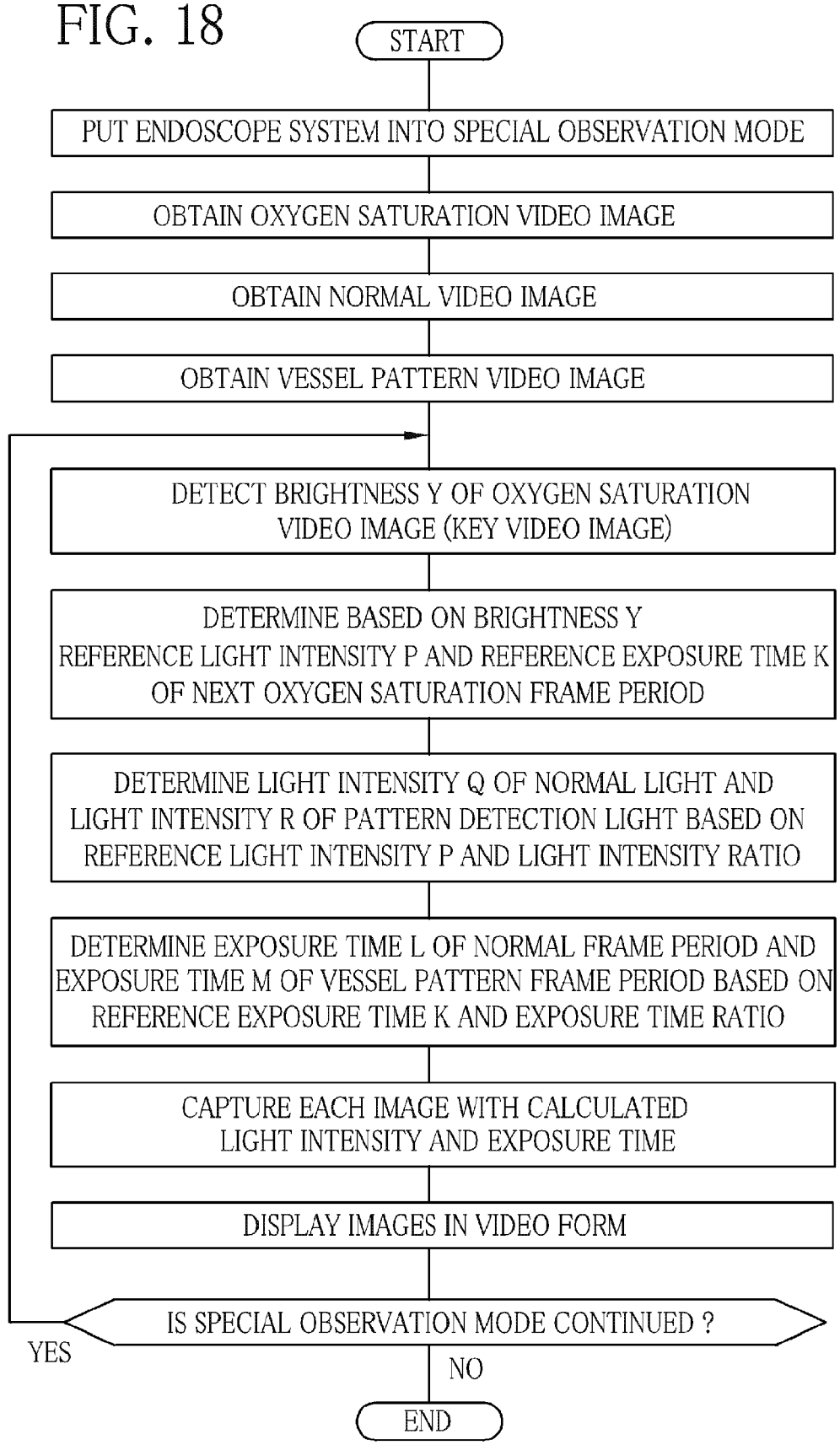
FIG. 18 is a flowchart of the special observation mode.

Next, the operation of the present invention will be described with referring to a flowchart of FIG. 18. The endoscope system 10 is put into the special observation mode by operation of the mode switch 21, and the oxygen saturation video image is assigned as the key video image. Thus, the oxygen saturation frame period is carried out, and the first and second measurement light is sequentially applied to the internal body portion. The oxygen saturation image is produced from the blue signal B1 of the first frame image and the green signal G2 and the red signal R2 of the second frame image obtained in the oxygen saturation frame period.

After that, the normal frame period is carried out, and the normal image is produced from the image signals B3, G3, and R3. Then, the vessel pattern frame period is carried out, and a vessel pattern image is produced from the image signals B4, G4, and R4.

Since the oxygen saturation video image is assigned as the key video image, information about the brightness Y of the first frame image is obtained. Based on the brightness Y, the light intensity P and the exposure time K of the first and second measurement light used for obtaining the next frame image set are determined. After that, the light intensity P is multiplied by the modification ratio Lb/La to obtain the light intensity Q of the normal light to be applied in the next normal frame period. The light intensity P is multiplied by the modification ratio Lc/La to obtain the light intensity R of the pattern detection light to be applied in the next vessel pattern frame period. The exposure time K is multiplied by the modification ratio Eb/Ea to obtain the exposure time L of the next normal frame period. The exposure time K is multiplied by the modification ratio Ec/Ea to obtain the exposure time M of the next vessel pattern frame period.

With the use of the light intensity P, Q, and R and the exposure time K, L, and M calculated as described above, the oxygen saturation frame period, the normal frame period, and the vessel pattern frame period are carried out. The obtained images are sequentially sent to the monitor 14 after being applied to the image processing. The monitor 14 displays the oxygen saturation video image, the normal video image, and the vessel pattern video image at the same time in predetermined sizes. The sequential operation described above is repeated as long as the endoscope system 10 stays in the special observation mode.

Second Embodiment

Figure 19:
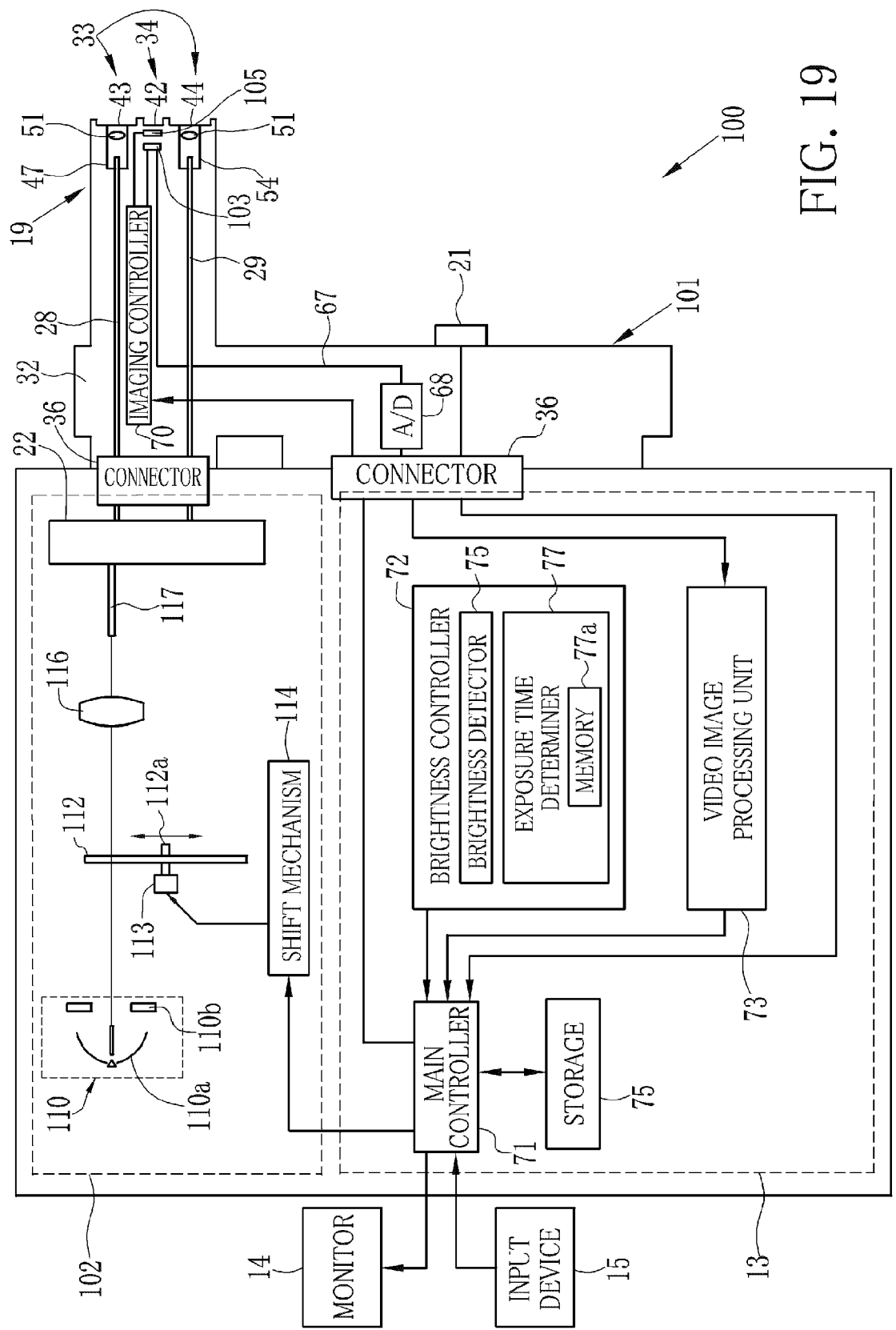
FIG. 19 is a block diagram of an endoscope system according to a second embodiment.

In the first embodiment, semiconductor light sources are used as the laser sources LD1 to LD3. Instead of this, a second embodiment adopts a rotary filter method in which broadband light from a white light source such as a xenon lamp is wavelength split. As shown in FIG. 19, an endoscope system 100 has the same structure as the endoscope system 10 of the first embodiment, except for an electronic endoscope 101 and a light source device 102. Therefore, the structure of the electronic endoscope 101 and the light source device 102 and parts related thereto will be described below, and explanation of the other parts will be omitted. Note that, it is difficult for the system of the second embodiment to perform control of the light intensity in a short time owing to the use of the rotary filter method. For this reason, the brightness controller 72 of the processor device 13 is not provided with the light intensity determiner 76.

The electronic endoscope 101 differs from the electronic endoscope 12 in terms that there is no phosphor 50 in the lighting section 33 provided in the head assembly 19. Thus, light from the light source device 102 is directly applied to the internal body portion as-is through the light guides 28 and 29. A monochrome CCD image sensor, which has no color filter in its imaging surface, is used as an image sensor 103, in contrast to the image sensor 60. A mechanical shutter 105 is provided between the image sensor 103 and the imaging window 42 to regulate exposure time. This mechanical shutter 105 is controlled by the imaging controller 70.

As for the other components, the electronic endoscope 101 has the same structure as the electronic endoscope 12. Note that, the mechanical shutter 105 is provided because a FT (frame transfer) type image sensor having no electronic shutter function is used as the image sensor 103. If an image sensor having the electronic shutter function is used as the image sensor 103, there is no need for providing the mechanical shutter 105.

The light source device 102 includes a white light source 110, a rotary filter unit 112, a motor 113, and a shift mechanism 114. The white light source 110 emits broadband light BB in wavelengths of 400 to 700 nm. The rotary filter unit 112 takes out light in a specific wavelength band from the broadband light BB emitted from the white light source 110. The motor 113 is connected to a rotary shaft 112a of the rotary filter unit 112, and rotates the rotary filter unit 112 at constant speed. The shift mechanism 114 shifts the rotary filter unit 112 in its radial direction.

The white light source 110 includes a main body 110a for emitting the broadband light BB and an aperture stop 110b for regulating the light amount of the broadband light BB. The main body 110a has a xenon lamp, a halogen lamp, a metal halide lamp, or the like. A light amount controller (not shown) regulates the degree of opening of the aperture stop 110b.

Figure 20:
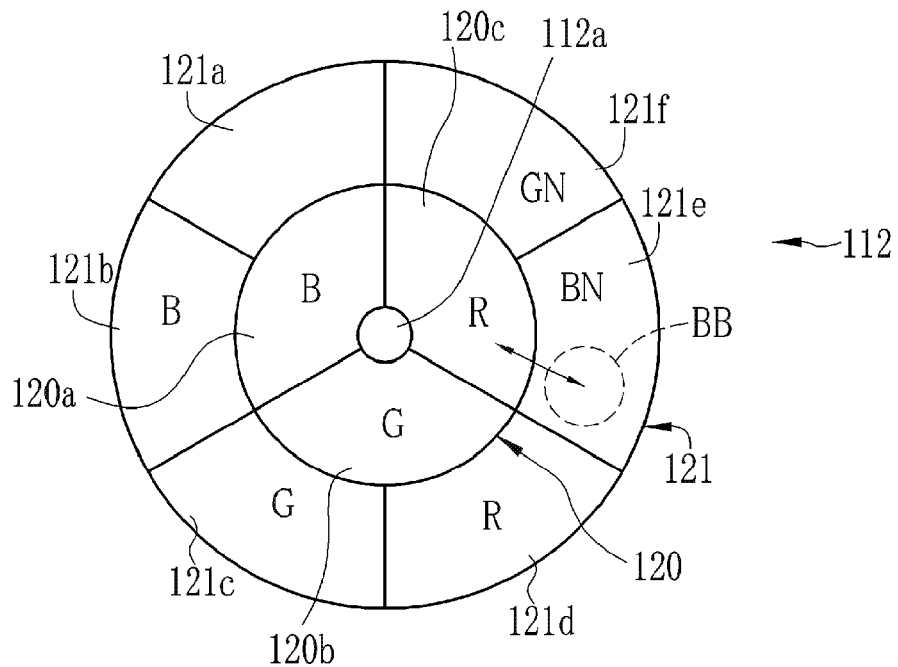
FIG. 20 is a plan view of a rotary filter unit.

As shown in FIG. 20, the rotary filter unit 112 rotates about the rotary shaft 112a connected to the motor 113. The rotary filter unit 112 is provided with a first filter area 120 and a second filter area 121, which are disposed in this order from the side of the rotary shaft 112a in its radial direction. The first filter area 120 is set in an optical path of the broadband light BB in the normal observation mode. The second filter area 121 is set in the optical path of the broadband light BB in the special observation mode. The shift mechanism 114 performs the switching in disposition between the first and second filter areas 120 and 121 by a shift of the rotary filter unit 112 in its radial direction.

Figure 21:
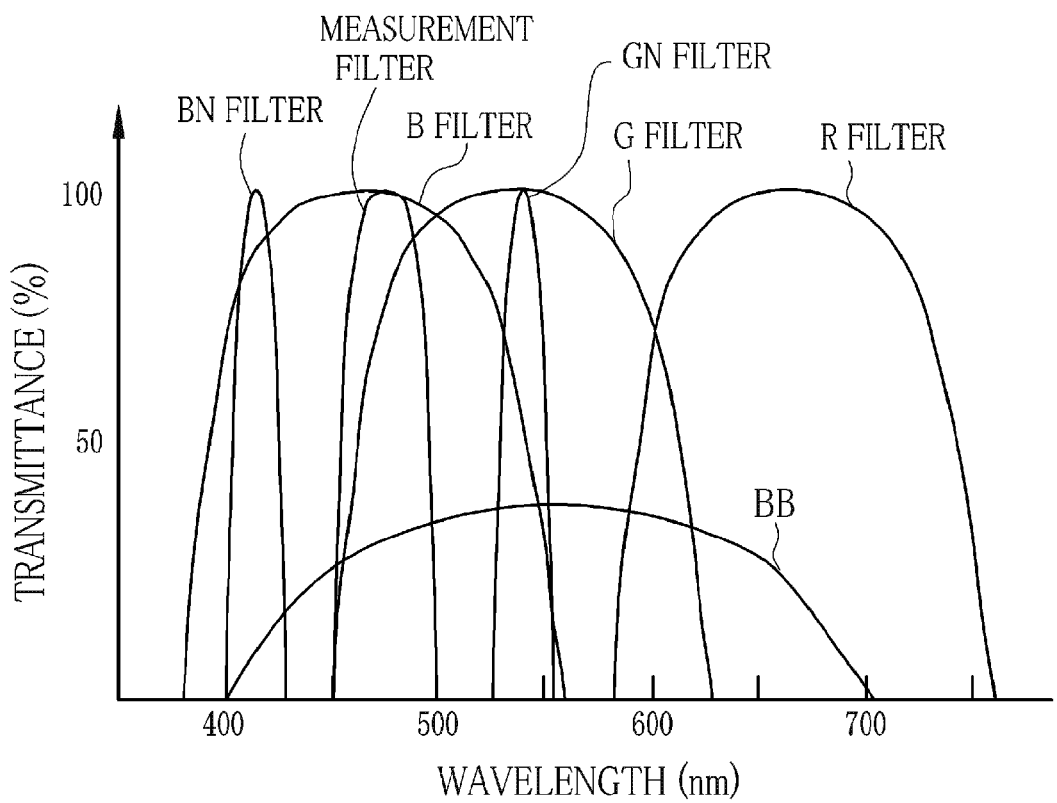
FIG. 21 is a graph showing spectral transmittance of each filter of the rotary filter unit.

The first filter area 120 has a B filter 120a, a G filter 120b, and an R filter 120c each of which has the shape of a sector having a central angle of 120°. As shown in FIG. 21, the B filter 120a transmits B light in a blue wavelength band (380 to 500 nm) out of the broadband light BB. The G filter 120b transmits G light in a green wavelength band (450 to 630 nm), and the R filter 120c transmits R light in a red wavelength band (580 to 760 nm) out of the broadband light BB. Thus, by the rotation of the rotary filter unit 112, the B light, the G light, and the R light extracted from the broadband light BB are emitted in a sequential manner. The B light, the G light, and the R light enters the light guides 28 and 29 through a condenser lens 116 and an optical fiber 117.

The second filter area 121 has a measurement filter 121a, a B filter 121b, and a G filter 121c, an R filter 121d, a BN filter 121e, and a GN filter 121f each of which has the shape of a sector having a central angle of 60°. The measurement filter 121a transmits oxygen saturation level measurement light (hereinafter simply called measurement light) in a wavelength range of 450 to 500 nm out of the broadband light BB. As with the B, G, and R filters 120a to 120c described above, the B filter 121b transmits the B light in the blue wavelength band (380 to 500 nm). The G filter 121c transmits the G light in the green wavelength band (450 to 630 nm), and the R filter 121d transmits the R light in the red wavelength band (580 to 760 nm).

The BN filter 121e transmits blue narrowband light (BN light) having a center wavelength of 415 nm. The GN filter 121f transmits green narrowband light (GN light) having a center wavelength of 540 nm. Therefore, by the rotation of the rotary filter unit 112, the measurement light, the B light, the G light, the R light, the BN light, and the GN light are taken out in a sequential manner. These six types of light sequentially enter the light guides 28 and 29 through the condenser lens 116 and the optical fiber 117.

Figure 22A:
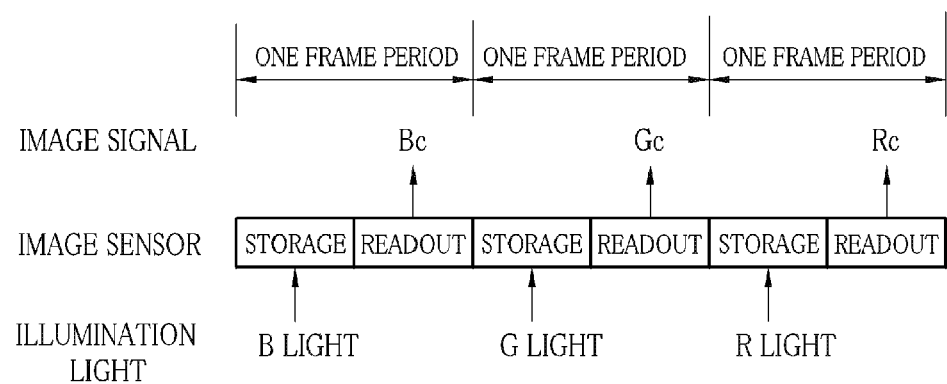
FIG. 22A is an explanatory view of imaging control in a normal observation mode of the second embodiment.

The imaging control of the endoscope system 100 is different from that of the endoscope system 10 due to the adoption of the rotary filter method. In the normal observation mode, as shown in FIG. 22A, the monochrome image sensor 103 captures B, G, and R colors of image light, and outputs a blue signal Bc, a green signal Gc, and a red signal Rc in a sequential manner. This operation is repeated while the endoscope system 100 stays in the normal observation mode. The normal video image is produced from the blue signal Bc, the green signal Gc, and the red signal Rc.

Figure 22B:
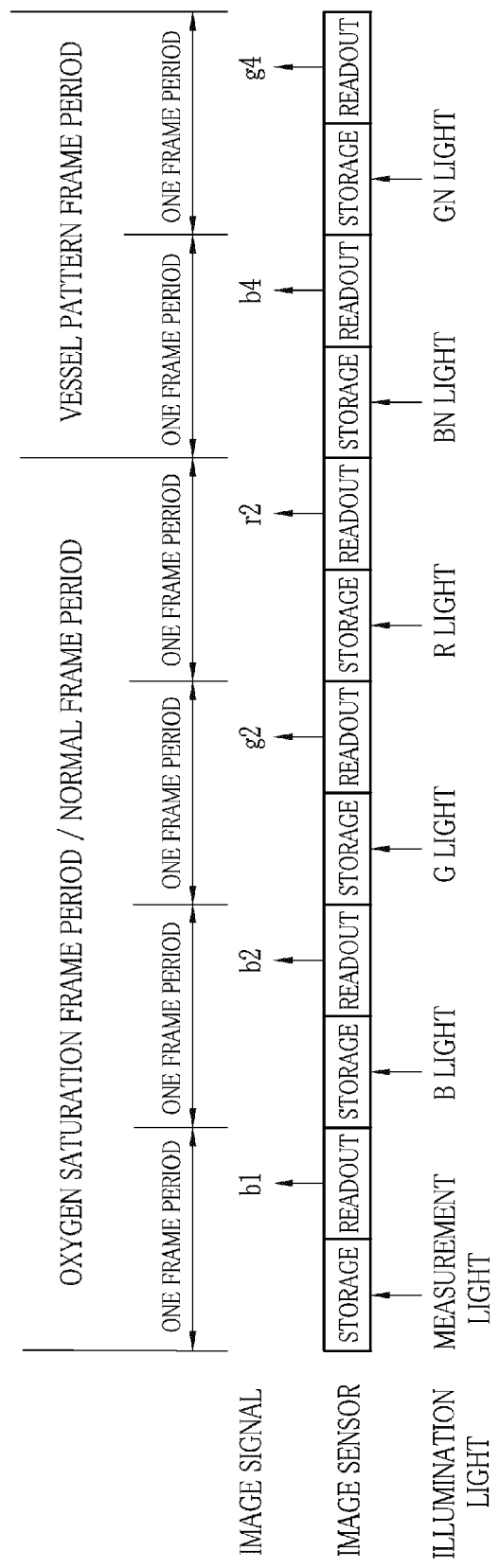
FIG. 22B is an explanatory view of imaging control in a special observation mode of the second embodiment.

In the special observation mode, as shown in FIG. 22B, the image sensor 103 captures the measurement light, the B light, the G light, the R light, the BN light, and the GN light, and outputs image signals in a sequential manner. This operation is repeated while the endoscope system 100 stays in the special observation mode. A signal b1 captured under the measurement light corresponds to the blue signal B1 of the first embodiment, because the signal b1 has a wavelength of 473 nm at which the absorption coefficient differs between the oxygenated hemoglobin and the deoxygenated hemoglobin.

A signal b2 captured under the B light corresponds to the blue signal B2 or B3 of the first embodiment, because the signal b2 is produced by photoelectric conversion of light in a blue wavelength band. A signal g2 captured under the G light corresponds to the green signal G2 or G3 of the first embodiment, because the signal g2 is produced by photoelectric conversion of light in a green wavelength band. A signal r2 captured under the R light corresponds to the red signal R2 or R3 of the first embodiment, because the signal r2 is based on light in a red wavelength band. A signal b4 captured under the BN light corresponds to the blue signal B4 of the first embodiment, because the signal b4 includes a blue component at a higher rate than the other components. A signal g4 captured under the GN light corresponds to the green signal G4 of the first embodiment that is used in producing the second vessel pattern image, because the signal g4 includes a green component at a higher rate than the other components.

In the second embodiment, the oxygen saturation video image is produced from the signals b1, g2, and r2. The normal video image is produced from the signals b2, g2, and r2. The vessel pattern video image is produced from the signals b4 and g4. The signals g2 and r2 are used for production of both the oxygen saturation image and the normal image. A method for producing the oxygen saturation video image, the normal video image, and the vessel pattern video image is the same as that of the first embodiment, so the description thereof will be omitted.

Figure 23:
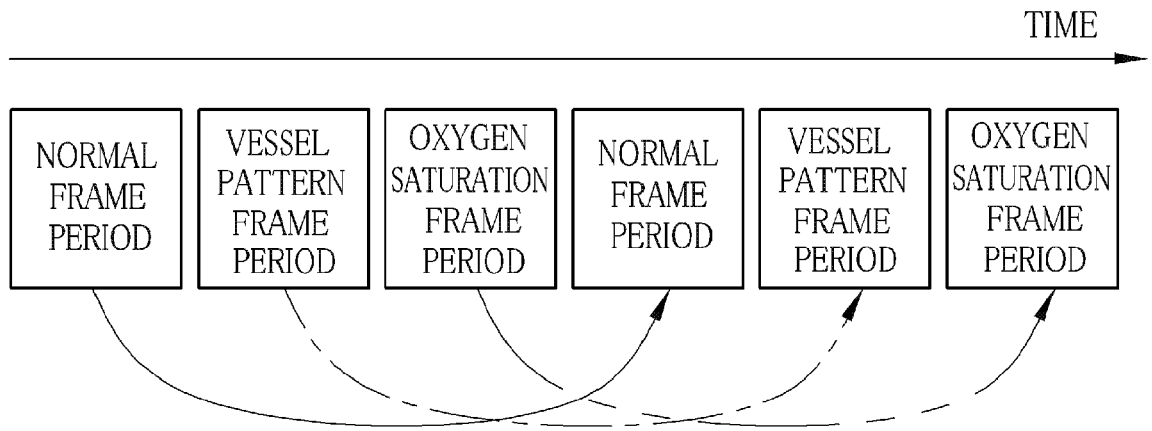
FIG. 23 is an explanatory view of a method for setting the light intensity and the exposure time according to another embodiment of the present invention.

In the above embodiments, the light intensity of each type of illumination light and the exposure time of each of the following four frame periods are determined based on the brightness of the latest frame image of the key video image. Instead of this, as shown in FIG. 23, the brightness of the latest frame image may be detected from one type of video image to another. Based on the detected brightness, the light intensity and the exposure time may be determined independently of the type of video image.

Figure 24:
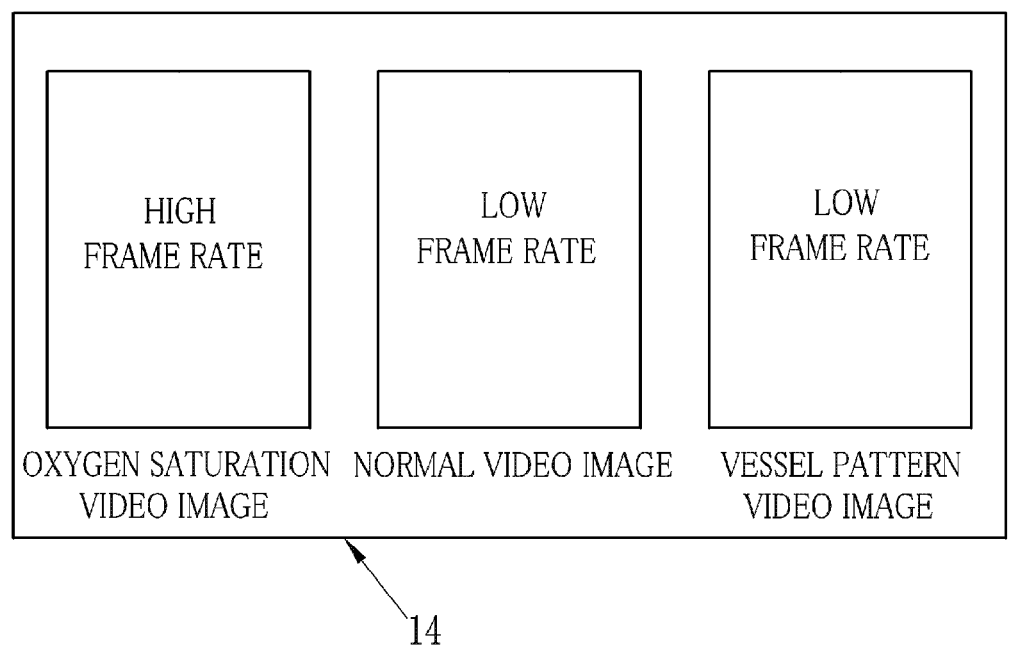
FIG. 24 is a plan view of the monitor in which the key video image has a frame rate higher than that of the other video images.

In the above embodiments, the key video image is displayed more brightly than the other video images in order to improve the visibility of the key video image (see FIG. 8A). Instead of this, as shown in FIG. 24, the key video image, for example, the oxygen saturation video image may have a higher frame rate than the other video images, to improve the visibility of the key video image.

In the above embodiment, the phosphor 50 is provided in the head assembly 19, but may be provided in the light source device 11. In this case, the phosphor 50 is necessarily disposed between the laser source LD2 (445 nm) and the optical fiber 25. The phosphor 50 is not necessarily disposed between the laser source LD1 (473 nm) and the optical fiber 24, and between the laser source LD3 (405 nm) and the optical fiber 26.

Note that, the oxygen saturation level is imaged in the present invention. However, an oxygenated hemoglobin index calculated by "blood volume (the sum of oxygenated hemoglobin and deoxygenated hemoglobin)×oxygen saturation level (%)" or a deoxygenated hemoglobin index calculated by "blood volume×(100−oxygen saturation level) (%)" may be imaged instead of or in addition to the oxygen saturation level.

Although the present invention has been fully described by the way of the preferred embodiment thereof with reference to the accompanying drawings, various changes and modifications will be apparent to those having skill in this field.

Therefore, unless otherwise these changes and modifications depart from the scope of the present invention, they should be construed as included therein.

What is claimed is:

1. An endoscope system comprising:
   a lighting section for sequentially and repeatedly applying a plurality of types of illumination light having different wavelength bands to an internal body portion;
   an image sensor for sequentially capturing reflected light from said internal body portion in each frame period in which said illumination light is applied, and producing a plurality of types of frame images corresponding to said types of illumination light;
   a video image processing unit for independently producing a plurality of modes of video images corresponding to said plurality of types of frame images, based on said plurality of types of frame images;
   a display section for displaying said plurality of modes of video images;
   a brightness detector for detecting brightness of a specific mode of video image out of said plurality of modes of video images;
   an exposure condition determiner having a memory for storing correlation in exposure conditions among said plurality of modes of video images, calculating said exposure condition of all of said plurality of modes of video images including said specific mode of video image based on said brightness detected by said brightness detector and said correlation, and determining exposure conditions of said plurality of modes of video images to said calculated conditions in a transition among said plurality of modes; and
      an exposure controller for regulating exposure of said image sensor in accordance with said determined exposure conditions.

2. The endoscope system according to claim 1, wherein said correlation in said exposure conditions is a light intensity ratio among said plurality of types of illumination light.

3. The endoscope system according to claim 1, wherein said correlation in said exposure conditions is an exposure time ratio of said image sensor to obtain each of said plurality of types of frame images.

4. The endoscope system according to claim 1, wherein said memory stores a first correlation for making visibility of a specific mode of video image produced from said plurality of modes of video images higher than that of the other modes of video images, and a second correlation for making visibility of two or more of said modes of video images including said specific mode of video image higher than that of the other modes of video images; and
   one of said first and second correlation is chosen manually.

5. The endoscope system according to claim 4, wherein said plurality of modes of video images produced with use of said first or second correlation have different brightness from each other.

6. The endoscope system according to claim 4, wherein said plurality of modes of video images produced with use of said first or second correlation have different frame rates from each other.

7. The endoscope system according to claim 1, wherein said plurality of modes of video images include:
   a normal video image obtained under white light;
   an oxygen saturation video image that images an oxygen saturation level of blood; and
   a vessel pattern video image that images a blood vessel pattern of specific depth.

8. The endoscope system according to claim 1, wherein said lighting section includes a plurality of semiconductor light sources for emitting said plurality of types of illumination light.

9. The endoscope system according to claim 1, wherein said lighting section includes:
   a broadband light source for emitting broadband light; and
   a wavelength splitter for splitting light in a specific wavelength band from said broadband light, to produce said plurality of types of illumination light.

10. A processor device of an endoscope system having a lighting section for sequentially and repeatedly applying a plurality of types of illumination light having different wavelength bands to an internal body portion, and an image sensor for sequentially capturing reflected light from said internal body portion in each frame period in which said illumination light is applied and producing a plurality of types of frame images corresponding to said types of illumination light, said processor device comprising:
   a video image processing unit for independently producing a plurality of modes of video images corresponding to said plurality of types of frame images, based on said plurality of types of frame images;
   a display section for displaying said plurality of modes of video images;
   a brightness detector for detecting brightness of a specific mode of video image out of said plurality of modes of video images;
   an exposure condition determiner having a memory for storing correlation in exposure conditions among said plurality of modes of video images, calculating said exposure condition of all of said plurality of modes of video images including said specific mode of video image based on said brightness detected by said brightness detector and said correlation, and determining exposure conditions of said plurality of modes of video images to said calculated conditions in a transition among said plurality of modes; and
   an exposure controller for regulating exposure of said image sensor in accordance with said determined exposure conditions.

11. An exposure control method of an endoscope system, the exposure control method comprising:
   sequentially and repeatedly applying a plurality of types of illumination light having different wavelength bands to an internal body portion;
   sequentially capturing reflected light from said internal body portion in each frame period in which said illumination light is applied, and producing a plurality of types of frame images corresponding to said types of illumination light;
   independently producing a plurality of modes of video images corresponding to said plurality of types of frame images, based on said plurality of types of frame images;
   displaying said plurality of modes of video images;
   detecting brightness of a specific mode of video image out of said plurality of modes of video images;
   storing correlation in exposure conditions among said plurality of modes of video images;
   calculating said exposure condition of all of said plurality of modes of video images including said specific mode of video image based on said brightness detected by said brightness detector and said correlation;
   determining exposure conditions of said plurality of modes of video images to said calculated conditions in a transition among said plurality of modes; and regulating exposure of said image sensor in accordance with said determined exposure conditions.

12. An endoscope system comprising:

a lighting section for sequentially and repeatedly applying oxygen saturation level measurement light including light in blue wavelength band and illumination light having a wavelength band different from said oxygen saturation level measurement light to an internal body portion;

an image sensor for capturing reflected light from said internal body portion in a frame period in which said oxygen saturation level measurement light is applied to produce an oxygen saturation frame image, and capturing reflected light from said internal body portion in a frame period in which said illumination light is applied to produce a normal frame image;

an oxygen saturation video image processing unit for producing an oxygen saturation video image based on said oxygen saturation frame image;

a normal video image processing unit for producing a normal video image based on said normal frame image;

a display section for displaying said oxygen saturation video image and said normal video image;

a brightness detector for detecting brightness of said oxygen saturation video image;

an exposure condition determiner having a memory for storing a correlation coefficient of exposure time between said oxygen saturation video image and said normal video image, calculating exposure time of said oxygen saturation video image based on said brightness of said oxygen saturation video image detected by said brightness detector, calculating exposure time of said normal video image by multiplying said exposure time of said oxygen saturation video image by said correlation coefficient, and determining exposure time of a video image of a transition destination to said calculated exposure time in a transition between said oxygen saturation video image and said normal video image; and an exposure controller for regulating exposure of said image sensor in accordance with said determined exposure time.

* * * * *